(12) United States Patent
Das et al.

(10) Patent No.: US 9,187,437 B2
(45) Date of Patent: *Nov. 17, 2015

(54) SUBSTITUTED OXADIAZOLE COMPOUNDS

(75) Inventors: Jagabandhu Das, Mercerville, NJ (US); Soo Sung Ko, Hockessin, DE (US)

(73) Assignee: BRISTOL-MYERS SQUIBB COMPANY, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/825,595

(22) PCT Filed: Sep. 23, 2011

(86) PCT No.: PCT/US2011/052876
§ 371 (c)(1),
(2), (4) Date: Mar. 22, 2013

(87) PCT Pub. No.: WO2012/040532
PCT Pub. Date: Mar. 29, 2012

(65) Prior Publication Data
US 2013/0190361 A1    Jul. 25, 2013

Related U.S. Application Data

(60) Provisional application No. 61/386,150, filed on Sep. 24, 2010.

(51) Int. Cl.
| | |
|---|---|
| C07D 271/06 | (2006.01) |
| C07D 271/12 | (2006.01) |
| C07D 413/00 | (2006.01) |
| C07D 498/00 | (2006.01) |
| C07D 413/04 | (2006.01) |
| C07D 413/14 | (2006.01) |
| A61K 31/44 | (2006.01) |
| A61K 31/41 | (2006.01) |
| C07D 413/10 | (2006.01) |
| C07D 413/12 | (2006.01) |
| C07D 417/04 | (2006.01) |
| C07D 417/12 | (2006.01) |

(52) U.S. Cl.
CPC ............ *C07D 271/06* (2013.01); *C07D 413/04* (2013.01); *C07D 413/10* (2013.01); *C07D 413/12* (2013.01); *C07D 417/04* (2013.01); *C07D 417/12* (2013.01)

(58) Field of Classification Search
None
See application file for complete search history.

(56) References Cited

U.S. PATENT DOCUMENTS

| | | | |
|---|---|---|---|
| 5,597,825 | A | 1/1997 | Himmelsbach et al. |
| 7,160,883 | B2 | 1/2007 | Dyckman et al. |
| 7,605,171 | B2 | 10/2009 | Colandrea et al. |
| 8,354,398 | B2 | 1/2013 | Watterson et al. |
| 8,389,509 | B2 | 3/2013 | Dyckman et al. |
| 8,399,451 | B2 | 3/2013 | Gilmore et al. |
| 8,404,672 | B2 | 3/2013 | Pitts et al. |
| 8,822,510 | B2 * | 9/2014 | Das et al. ............ 514/364 |
| 2004/0072880 | A1 * | 4/2004 | Lloyd et al. ............ 514/362 |
| 2008/0113961 | A1 | 5/2008 | Nishi et al. |
| 2008/0200535 | A1 | 8/2008 | Komatsu et al. |
| 2009/0076070 | A1 | 3/2009 | Harada et al. |
| 2012/0214767 | A1 | 8/2012 | Dhar et al. |
| 2013/0045964 | A1 | 2/2013 | Cherney et al. |
| 2013/0158001 | A1 * | 6/2013 | Das et al. ............ 514/210.18 |

FOREIGN PATENT DOCUMENTS

| | | |
|---|---|---|
| WO | WO03/061567 | 7/2003 |
| WO | WO03/062248 | 7/2003 |
| WO | WO03/062252 | 7/2003 |
| WO | WO03/073986 | 9/2003 |
| WO | WO03/105771 | 12/2003 |
| WO | WO2004/058149 | 7/2004 |
| WO | WO2004/071442 | 8/2004 |
| WO | WO2004/103279 | 12/2004 |

(Continued)

OTHER PUBLICATIONS

Gupta, BD. et al. Cobaloximes with Bis(thiophenyl)glyoxime: Synthesis and Structure-Property Relationship Study. Organometallics. 2009, vol. 28, p. 3486.*

(Continued)

*Primary Examiner* — Rita Desai
*Assistant Examiner* — Ben S Michelson
(74) *Attorney, Agent, or Firm* — Gary D. Greenblatt

(57) ABSTRACT

Disclosed are compounds of Formula (I):

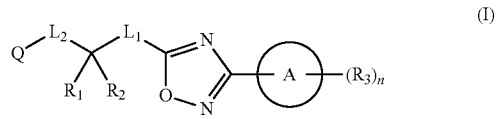

or stereoisomers, N-oxides, salts, or prodrugs thereof; wherein: Ring A is phenyl or 5- to 6-membered heteroaryl; (i) R1 and R2 are independently C1-C4 alkyl; or (ii) R1 and R2 together with the carbon atom to which they are attached, form a cyclic group; Q is phenyl or 5- to 6-membered heteroaryl substituted with zero to 3 substituents; and R3, L1, L2, and n are defined herein. Also disclosed are methods of using such compounds as selective agonists for G protein-coupled receptor S1P1, and pharmaceutical compositions comprising such compounds. These compounds are useful in treating, preventing, or slowing the progression of diseases or disorders in a variety of therapeutic areas, such as autoimmune diseases and vascular disease.

7 Claims, No Drawings

(56) References Cited

FOREIGN PATENT DOCUMENTS

| WO | WO2004/103306 | 12/2004 |
|---|---|---|
| WO | WO2004/103309 | 12/2004 |
| WO | WO2004/113330 | 12/2004 |
| WO | WO2005/000833 | 1/2005 |
| WO | WO2005/014525 | 2/2005 |
| WO | WO2005/032465 | 4/2005 |
| WO | WO2005/058848 | 6/2005 |
| WO | WO2005/077345 | 8/2005 |
| WO | WO2005/082089 | 9/2005 |
| WO | WO2006/047195 | 5/2006 |
| WO | WO2006/100631 | 9/2006 |
| WO | WO2006/100633 | 9/2006 |
| WO | WO2006/131336 | 12/2006 |
| WO | WO2006/137019 | 12/2006 |
| WO | WO2007/024922 | 3/2007 |
| WO | WO2007/061458 | 5/2007 |
| WO | WO2007/080542 | 7/2007 |
| WO | WO2007/085451 | 8/2007 |
| WO | WO2007/091396 | 8/2007 |
| WO | WO2007/109330 | 9/2007 |
| WO | WO2007/116866 | 10/2007 |
| WO | WO2007/132307 | 11/2007 |
| WO | WO2008/016674 | 2/2008 |
| WO | WO2008/028937 | 3/2008 |
| WO | WO2008/029306 | 3/2008 |
| WO | WO2008/029370 | 3/2008 |
| WO | WO2008/029371 | 3/2008 |
| WO | WO2008/030843 | 3/2008 |
| WO | WO2008/035239 | 3/2008 |
| WO | WO2008/037476 | 4/2008 |
| WO | WO2008/064315 | 5/2008 |
| WO | WO2008/074820 | 6/2008 |
| WO | WO2008/074821 | 6/2008 |
| WO | WO2008/076356 | 6/2008 |
| WO | WO 2008074820 A1 * | 6/2008 |
| WO | WO2008/079382 | 7/2008 |
| WO | WO2008/091967 | 7/2008 |
| WO | WO2008/114157 | 9/2008 |
| WO | WO2009/011850 | 1/2009 |
| WO | WO2009/043889 | 4/2009 |
| WO | WO2009/043890 | 4/2009 |
| WO | WO 2009/043890 A1 * | 4/2009 |
| WO | WO2009/057079 | 5/2009 |
| WO | WO2009/074950 | 6/2009 |
| WO | WO2010/033701 | 3/2010 |
| WO | WO2010/142628 | 12/2010 |
| WO | WO2012/012477 | 1/2012 |
| WO | WO2012/061459 | 5/2012 |

OTHER PUBLICATIONS

Bettencourt-Dias, AD. et al. Eu(III) and Tb(III) Luminescence Sensitized by Thiophenyl-Derivatized Nitrobenzoato Antennas. Inorganic Chemistry. 2006, vol. 45, p. 10139.*

Carey, FA. Organic Chemistry 6th Ed. McGraw Hill. 2006, chapter 1, p. 9.*

Newton, R. Maybridge MedChem Bioisosteres in Medicinal Chemistry. Maybridge. 2004, vol. 1, p. 16.*

Hale, J.J., et al. "A Rational Utilization of High-Throughput Screening Affords Selective, Orally Bioavailable 1-Benzyl-3-carboxyazetidine Sphingosine-1-phosphate-1 Receptor Agonists" J Med Chem 47, 6662-5 (2004).

PCT Search Report for PCT/US2011/052876 issued Mar. 26, 2013.

* cited by examiner

SUBSTITUTED OXADIAZOLE COMPOUNDS

DESCRIPTION

The present invention generally relates to substituted oxadiazole compounds useful as $S1P_1$ agonists. Provided herein are substituted oxadiazole compounds, compositions comprising such compounds, and methods of their use. The invention further pertains to pharmaceutical compositions comprising at least one compound according to the invention that are useful for the treatment of conditions related to $S1P_1$ agonism, such as autoimmune diseases and vascular disease.

Sphingosine-1-phosphate (S1P) has been demonstrated to induce many cellular effects, including those that result in platelet aggregation, cell proliferation, cell morphology, tumor cell invasion, endothelial cell and leukocyte chemotaxis, endothelial cell in vitro angiogenesis, and lymphocyte trafficking. S1P receptors are therefore good targets for a wide variety of therapeutic applications such as tumor growth inhibition, vascular disease, and autoimmune diseases. S1P signals cells in part via a set of G protein-coupled receptors named $S1P_1$ or S1P1, $S1P_2$ or S1P2, $S1P_3$ or S1P3, $S1P_4$ or S1P4, and $S1P_5$ or S1P5 (formerly called EDG-1, EDG-5, EDG-3, EDG-6, and EDG-8, respectively).

S1P is important in the entire human body as it is also a major regulator of the vascular and immune systems. In the vascular system, S1P regulates angiogenesis, vascular stability, and permeability. In the immune system, S1P is recognized as a major regulator of trafficking of T- and B-cells. S1P interaction with its receptor $S1P_1$ is needed for the egress of immune cells from the lymphoid organs (such as thymus and lymph nodes) into the lymphatic vessels. Therefore, modulation of S1P receptors was shown to be critical for immunomodulation, and S1P receptor modulators are novel immunosuppressive agents.

The $S1P_1$ receptor is expressed in a number of tissues. It is the predominant family member expressed on lymphocytes and plays an important role in lymphocyte trafficking. Down-regulation of the $S1P_1$ receptor disrupts lymphocyte migration and homing to various tissues. This results in sequestration of the lymphocytes in lymph organs thereby decreasing the number of circulating lymphocytes that are capable of migration to the affected tissues. Thus, development of an $S1P_1$ receptor agent that suppresses lymphocyte migration to the target sites associated with autoimmune and aberrant inflammatory processes could be efficacious in a number of autoimmune and inflammatory disease states.

Among the five S1P receptors, $S1P_1$ has a widespread distribution and is highly abundant on endothelial cells where it works in concert with $S1P_3$ to regulate cell migration, differentiation, and barrier function. Inhibition of lymphocyte recirculation by non-selective S1P receptor modulation produces clinical immunosuppression preventing transplant rejection, but such modulation also results in transient bradycardia. Studies have shown that $S1P_1$ activity is significantly correlated with depletion of circulating lymphocytes. In contrast, $S1P_3$ receptor agonism is not required for efficacy. Instead, $S1P_3$ activity plays a significant role in the observed acute toxicity of nonselective S1P receptor agonists, resulting in the undesirable cardiovascular effects, such as bradycardia and hypertension. (See, e.g., Hale et al., *Bioorg. Med. Chem. Lett.*, 14:3501 (2004); Sanna et al., *J. Biol. Chem.*, 279:13839 (2004); Anliker et al., *J. Biol. Chem.*, 279:20555 (2004); Mandala et al., *J. Pharmacol. Exp. Ther.*, 309:758 (2004).).

An example of an $S1P_1$ agonist is FTY720. This immunosuppressive compound FTY720 (JPI 1080026-A) has been shown to reduce circulating lymphocytes in animals and humans, and to have disease modulating activity in animal models of organ rejection and immune disorders. The use of FTY720 in humans has been effective in reducing the rate of organ rejection in human renal transplantation and increasing the remission rates in relapsing remitting multiple sclerosis (see Brinkman et al., *J. Biol. Chem.*, 277:21453 (2002); Mandala et al., *Science*, 296:346 (2002); Fujino et al., *J. Pharmacol. Exp. Ther.*, 305:45658 (2003); Brinkman et al., *Am. J. Transplant.*, 4:1019 (2004); Webb et al., *J. Neuroimmunol.*, 153:108 (2004); Morris et al., *Eur. J. Immunol.*, 35:3570 (2005); Chiba, *Pharmacology & Therapeutics*, 108:308 (2005); Kahan et al., *Transplantation*, 76:1079 (2003); and Kappos et al., *N. Engl. J. Med.*, 335:1124 (2006)). Subsequent to its discovery, it has been established that FTY720 is a prodrug, which is phosphorylated in vivo by sphingosine kinases to a more biologically active agent that has agonist activity at the $S1P_1$, $S1P_3$, $S1P_4$, and $S1P_5$ receptors. It is this activity on the S1P family of receptors that is largely responsible for the pharmacological effects of FTY720 in animals and humans.

Clinical studies have demonstrated that treatment with FTY720 results in bradycardia in the first 24 hours of treatment (Kappos et al., *N. Engl. J. Med.*, 335:1124 (2006)). The observed bradycardia is commonly thought to be due to agonism at the $S1P_3$ receptor. This conclusion is based on a number of cell based and animal experiments. These include the use of $S1P_3$ knockout animals which, unlike wild type mice, do not demonstrate bradycardia following FTY720 administration and the use of $S1P_1$ selective compounds. (Hale et al., *Bioorg. Med. Chem. Lett.*, 14:3501 (2004); Sanna et al., *J. Biol. Chem.*, 279:13839 (2004); and Koyrakh et al., *Am. J. Transplant.*, 5:529 (2005)).

The following applications have described compounds as $S1P_1$ agonists: WO 03/061567 (U.S. Patent Publication No. 2005/0070506), WO 03/062248 (U.S. Pat. No. 7,351,725), WO 03/062252 (U.S. Pat. No. 7,479,504), WO 03/073986 (U.S. Pat. No. 7,309,721), WO 03/105771, WO 05/058848, WO 05/000833, WO 05/082089 (U.S. Patent Publication No. 2007/0203100), WO 06/047195, WO 06/100633, WO 06/115188, WO 06/131336, WO 2007/024922, WO 07/109,330, WO 07/116,866, WO 08/023,783 (U.S. Patent Publication No. 2008/0200535), WO 08/029,370, WO 08/114,157, WO 08/074,820, WO 09/043,889, WO 09/057,079, and U.S. Pat. No. 6,069,143. Also see Hale et al., *J. Med. Chem.*, 47:6662 (2004).

There still remains a need for compounds useful as $S1P_1$ agonists.

Applicants have found potent compounds that have activity as $S1P_1$ agonists. These compounds are provided to be useful as pharmaceuticals with desirable stability, bioavailability, therapeutic index, and toxicity values that are important to their drugability.

SUMMARY OF THE INVENTION

The present invention provides substituted oxadiazole compounds, which are useful as modulators of $S1P_1$ activity, including stereoisomers, N-oxides, salts, or prodrugs.

The present invention also provides processes and intermediates for making the compounds of the present invention or stereoisomers, N-oxides, salts, or prodrugs thereof.

The present invention also provides pharmaceutical compositions comprising a compound of Formula (I), or stereoisomers, N-oxides, pharmaceutically acceptable salts, or prodrugs thereof; and a pharmaceutically acceptable carrier.

The present invention also provides a method of treating a disease or disorder associated with the activity of G protein-coupled receptor S1P₁, the method comprising administering to a mammalian patient a compound of Formula (I) or stereoisomers, N-oxides, pharmaceutically acceptable salts, or prodrugs thereof.

The present invention also provides the compounds of the present invention or stereoisomers, N-oxides, pharmaceutically acceptable salts, or prodrugs thereof, for use in therapy.

The present invention also provides the use of the compounds of the present invention or stereoisomers, N-oxides, pharmaceutically acceptable salts, or prodrugs thereof, for the manufacture of a medicament for the treatment or prophylaxis of S1P₁ receptor-related conditions, such as autoimmune and vascular diseases.

The compounds of Formula (I) and compositions comprising the compounds are S1P₁ agonists. The compounds of Formula (I) and compositions comprising said compounds may be used in treating, preventing or curing various S1P₁ receptor-related conditions while reducing or minimizing the side effects due to S1P₃ activity. Pharmaceutical compositions comprising these compounds are useful in treating, preventing, or slowing the progression of diseases or disorders in a variety of therapeutic areas, such as autoimmune and vascular diseases.

DETAILED DESCRIPTION

In a first aspect, the present invention provides compounds of Formula (I):

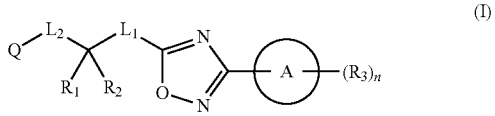

or stereoisomers, N-oxides, salts, or prodrugs thereof; wherein:
Ring A is phenyl or 5- to 6-membered heteroaryl;
(i) $R_1$ and $R_2$ are independently $C_1$-$C_4$ alkyl; or
(ii) $R_1$ and $R_2$ together with the carbon atom to which they are attached, form a cyclic group selected from adamantanyl, bicyclo[2.2.1]heptanyl, bicyclo[2.2.2]octanyl, $C_{3-7}$cycloalkyl, and a 4- to 6-membered heterocycloalkyl, wherein each of said cycloalkyl and heterocycloalkyl rings is substituted with zero to 4 $R_a$;
each $R_3$ is independently:
(i) F, Cl, $C_{1-4}$alkyl, —CF₃, —O($C_{1-4}$alkyl), —OCF₃, —S(O)$_m$($C_{1-4}$alkyl), and/or —NH₂; and/or
(ii) —CH₂A₁, —OA₁, —OCH₂A₁, —CH₂OA₁, and/or —CH₂SO₂A₁, wherein A₁ is phenyl, pyridinyl, thiazolyl, or imidazolyl substituted with zero to 2 substituents independently selected from F, Cl, —NH₂, $C_{1-4}$alkyl, —CF₃, $C_{1-4}$alkoxy, and/or —S($C_{1-4}$alkyl);
$L_1$ is:
  (a) —(CR$_b$R$_b$)$_{2-4}$—,
  (b) —(CH₂)$_{0-3}$—CR$_c$═CR$_c$—(CH₂)$_{0-3}$, or
  (c) —(CH₂)$_{0-3}$O(CH₂)$_{1-3}$— or —(CH₂)$_{0-3}$S(CH₂)$_{1-3}$—;
$L_2$ is:
  (a) a bond,
  (b) —(CR$_b$R$_b$)$_{1-4}$—,
  (c) —(CH₂)$_{0-3}$—CR$_c$═CR$_c$—(CH₂)$_{0-3}$, or
  (d)-(CH₂)$_{0-3}$O(CH₂)$_{1-3}$— or —(CH₂)$_{0-3}$S(CH₂)$_{1-3}$—;
Q is phenyl or 5- to 6-membered heteroaryl substituted with zero to 3 substituents independently selected from F, Cl, $C_{1-3}$alkyl, —CN, —NO₂, —NH₂, $C_{1-2}$fluoroalkyl, $C_{1-3}$alkoxy, $C_{1-2}$fluoroalkoxy, —NHC(O)($C_{1-3}$alkyl), —NHC(O)O($C_{1-3}$alkyl), —NHS(O)₂($C_{1-3}$alkyl), and/or —S($C_{1-3}$alkyl);
each $R_a$ is independently F, Cl, $C_{1-3}$alkyl, and/or —S(O)₂$R_d$; and/or two $R_a$ attached to the same carbon atom form ═O;
each $R_b$ is independently H, —CH₃, F, Cl, —OH, and/or $C_{1-3}$alkoxy, provided that if one $R_b$ is —OH, then the second $R_b$ attached to the same carbon is not —OH, F, or Cl;
each $R_c$ is independently H, F, and/or $C_{1-2}$alkyl;
$R_d$ is phenyl substituted with zero to 2 substituents independently selected from F, Cl, —CH₃, —CF₃, —OCH₃, and/or —OCF₃;
m is zero, 1, or 2; and
n is zero, 1, 2, or 3.

One embodiment provides a compound of Formula (I) or stereoisomers, N-oxides, salts, or prodrugs thereof, wherein $R_1$ and $R_2$ are independently $C_1$-$C_4$ alkyl; preferably $R_1$ is —CH₃ and $R_2$ is $C_{1-4}$alkyl; and preferably, $R_1$ is —CH₃ and $R_2$ is $C_{1-2}$alkyl. Included in this embodiment are compounds of Formula (I) in which $R_1$ is —CH₃ and $R_2$ is —CH₃.

One embodiment provides a compound of Formula (I) or stereoisomers, N-oxides, salts, or prodrugs thereof, wherein $R_1$ and $R_2$ together with the carbon atom to which they are attached, form a cyclic group selected from adamantanyl, bicyclo[2.2.1]heptanyl, bicyclo[2.2.2]octanyl, $C_{3-7}$cycloalkyl, and a 4- to 6-membered heterocycloalkyl, wherein each of said cycloalkyl and heterocycloalkyl rings is substituted with zero to 4 $R_a$; and preferably, $R_1$ and $R_2$ together with the carbon atom to which they are attached, form a cyclic group selected from $C_{3-7}$cycloalkyl and a 4- to 6-membered heterocycloalkyl, wherein each of said cycloalkyl and heterocycloalkyl rings is substituted with zero to 4 $R_a$. Each $R_a$ is independently F, Cl, $C_{1-3}$alkyl, and/or —S(O)₂$R_d$; and/or two $R_a$ attached to the same carbon atom form ═O. Included in this embodiment are compounds of Formula (I) in which each $R_a$ is independently F, Cl, and/or —CH₃; and/or two $R_a$ attached to the same carbon atom form ═O.

One embodiment provides a compound of Formula (I) or stereoisomers, N-oxides, salts, or prodrugs thereof, wherein $R_1$ and $R_2$ together with the carbon atom to which they are attached, form a cyclic group selected from adamantanyl, bicyclo[2.2.1]heptanyl, and bicyclo[2.2.2]octanyl.

One embodiment provides a compound of Formula (I) or stereoisomers, N-oxides, salts, or prodrugs thereof, wherein $R_1$ and $R_2$ together with the carbon atom to which they are attached, form a cyclic group selected from $C_{3-7}$cycloalkyl and a 4- to 6-membered heterocycloalkyl; preferably a cyclic group selected from $C_{3-6}$cycloalkyl and a 5- to 6-membered heterocycloalkyl; wherein each of said cycloalkyl and heterocycloalkyl rings is substituted with zero to 4 $R_a$.

One embodiment provides a compound of Formula (I) or stereoisomers, N-oxides, salts, or prodrugs thereof, wherein $R_1$ and $R_2$ together with the carbon atom to which they are attached, form a $C_{3-6}$cycloalkyl substituted with zero to 4 $R_a$. Examples of suitable cycloalkyl groups include cyclopropyl, cyclobutyl, cyclopentyl, and cyclohexyl groups.

One embodiment provides a compound of Formula (I) or stereoisomers, N-oxides, salts, or prodrugs thereof, wherein $R_1$ and $R_2$ together with the carbon atom to which they are attached, form a 4- to 6-membered heterocycloalkyl; preferably a 5- to 6-membered heterocycloalkyl; substituted with zero to 4 $R_a$. Examples of suitable heterocycloalkyl groups include pyrrolidine, piperidine, tetrahydrofuran, and tetrahydropyran.

One embodiment provides a compound of Formula (I) or stereoisomers, N-oxides, salts, or prodrugs thereof, wherein n is zero, 1, 2, or 3; and each $R_3$ is independently F, Cl, $C_{1-4}$alkyl, —$CF_3$, —$O(C_{1-3}$alkyl), —$OCF_3$, —$S(O)_m$($C_{1-2}$alkyl), and/or —$NH_2$; and/or —$CH_2A_1$, —$OA_1$, —$OCH_2A_1$, —$CH_2OA_1$, and/or —$CH_2SO_2A_1$, wherein $A_1$ is phenyl, pyridinyl, thiazolyl, or imidazolyl substituted with zero to 2 substituents independently selected from F, Cl, —$NH_2$, $C_{1-3}$alkyl, —$CF_3$, and/or $C_{1-2}$alkoxy. Included in this embodiment are compounds in which n is zero, 1, or 2.

One embodiment provides a compound of Formula (I) or stereoisomers, N-oxides, salts, or prodrugs thereof, wherein n is zero, 1, 2, or 3; preferably n is zero, 1, or 2; and each $R_3$ is independently F, Cl, $C_{1-4}$alkyl, —$CF_3$, —$O(C_{1-3}$alkyl), —$OCF_3$, —$S(O)_m(C_{1-2}$alkyl), and/or —$NH_2$; preferably each $R_3$ is independently F, Cl, $C_{1-4}$alkyl, —$CF_3$, —$O(C_{1-2}$alkyl), —$OCF_3$, and/or —$NH_2$. Included in this embodiment are compounds in which each $R_3$ is independently F, Cl, $C_{1-4}$alkyl, —$CF_3$, —$OCH_3$, —$OCF_3$, and/or —$NH_2$.

One embodiment provides a compound of Formula (I) or stereoisomers, N-oxides, salts, or prodrugs thereof, wherein n is 1; and $R_3$ is $CH_2A_1$, —$OA_1$, —$OCH_2A_1$, —$CH_2OA_1$, and/or —$CH_2SO_2A_1$, wherein $A_1$ is phenyl, pyridinyl, thiazolyl, or imidazolyl substituted with zero to 2 substituents independently selected from F, Cl, —$NH_2$, $C_{1-3}$alkyl, —$CF_3$, and/or $C_{1-2}$alkoxy.

One embodiment provides a compound of Formula (I) or stereoisomers, N-oxides, salts, or prodrugs thereof, wherein n is 2; and one $R_3$ is $CH_2A_1$, —$OA_1$, —$OCH_2A_1$, —$CH_2OA_1$, and/or —$CH_2SO_2A_1$, wherein $A_1$ is phenyl, pyridinyl, thiazolyl, or imidazolyl substituted with zero to 2 substituents independently selected from F, Cl, —$NH_2$, $C_{1-3}$alkyl, —$CF_3$, and/or $C_{1-2}$alkoxy; and the second $R_3$ is F, Cl, $C_{1-4}$alkyl, —$CF_3$, —$O(C_{1-3}$alkyl), —$OCF_3$, —$S(O)_m(C_{1-2}$alkyl), or —$NH_2$.

One embodiment provides a compound of Formula (I) or stereoisomers, N-oxides, salts, or prodrugs thereof, wherein $L_1$ is —$(CR_bR_b)_{2-4}$—, —$(CH_2)_{0-2}$—$CR_c$=$CR_c$—$(CH_2)_{0-2}$, or —$(CH_2)_{0-2}O(CH_2)_{1-2}$—. Included in this embodiment are compounds in which $L_1$ is —$(CR_bR_b)_{2-4}$— or —$(CH_2)_{0-2}O(CH_2)_{1-2}$—. Also included in this embodiment are compounds in which $L_1$ is —$(CR_bR_b)_{2-4}$—, including, for example, $L_1$ is —$CH_2CH_2$—.

One embodiment provides a compound of Formula (I) or stereoisomers, N-oxides, salts, or prodrugs thereof, wherein $L_2$ is a bond, —$(CR_bR_b)_{1-4}$—, —$(CH_2)_{0-2}$—$CR_c$=$CR_c$—$(CH_2)_{0-2}$, or —$(CH_2)_{0-2}O(CH_2)_{1-2}$—. Included in this embodiment are compounds in which $L_2$ is a bond, —$(CR_bR_b)_{1-4}$—, or —$(CH_2)_{0-2}O(CH_2)_{1-2}$—. Also included in this embodiment are compounds in which $L_2$ is a bond or —$(CR_bR_b)_{1-4}$—; and compounds in which $L_2$ is a bond or —$(CH_2)_{1-4}$—.

One embodiment provides a compound of Formula (I) or stereoisomers, N-oxides, salts, or prodrugs thereof, wherein Q is phenyl or 5- to 6-membered heteroaryl substituted with zero to 3 substituents independently selected from F, Cl, $C_{1-3}$alkyl, —$CN$, —$NO_2$, —$NH_2$, —$CF_3$, $C_{1-2}$alkoxy, and/or —$OCF_3$. Included in this embodiment are compounds in which Q is phenyl or 5- to 6-membered heteroaryl substituted with zero to 3 substituents independently selected from F, Cl, $C_{1-2}$alkyl, —$CN$, —$NH_2$, —$CF_3$, —$OCH_3$, and/or —$OCF_3$.

One embodiment provides a compound of Formula (I) or stereoisomers, N-oxides, salts, or prodrugs thereof, wherein Q is phenyl substituted with zero to 3 substituents independently selected from F, Cl, —$CH_3$, —$CN$, and/or —$CF_3$. Included in this embodiment are compounds in which Q is phenyl substituted with zero to 2 substituents selected from F, Cl, —$CH_3$, —$CN$, and/or —$CF_3$.

One embodiment provides a compound of Formula (I) or stereoisomers, N-oxides, salts, or prodrugs thereof, wherein Q is a 5- to 6-membered heteroaryl substituted with zero to 3 substituents independently selected from F, Cl, $C_{1-3}$alkyl, —$CN$, —$NO_2$, —$NH_2$, —$CF_3$, $C_{1-2}$alkoxy, and/or —$OCF_3$. Included in this embodiment are compounds in which Q is a 5-membered heteroaryl substituted with zero to 3 substituents independently selected from F, Cl, $C_{1-2}$alkyl, —$CN$, —$NH_2$, —$CF_3$, —$OCH_3$, and/or —$OCF_3$. Suitable 5-membered heteroaryl groups include, for example, pyrrolyl, thiophenyl, pyrazolyl, imidazolyl, isoxazolyl, and thiazolyl. Also included in this embodiment are compounds in which Q is a 6-membered heteroaryl substituted with zero to 3 substituents independently selected from F, Cl, $C_{1-2}$alkyl, —$CN$, —$NH_2$, —$CF_3$, —$OCH_3$, and/or —$OCF_3$. Suitable 6-membered heteroaryl groups include, for example, pyridinyl, pyridazinyl, and pyrimidinyl.

One embodiment provides a compound of Formula (I) or stereoisomers, N-oxides, salts, or prodrugs thereof, wherein:
Ring A is phenyl or 5- to 6-membered heteroaryl having at least one N or S heteroatom;
(i) $R_1$ and $R_2$ are independently $C_{1-3}$alkyl; or
(ii) $R_1$ and $R_2$ together with the carbon atom to which they are attached, form a cyclic group selected from $C_{3-7}$cycloalkyl and 4- to 6-membered heterocycloalkyl, wherein each of said cycloalkyl and heterocycloalkyl rings is substituted with zero to 4 $R_a$;
each $R_3$ is independently:
(i) F, Cl, $C_{1-4}$alkyl, —$CF_3$, —$O(C_{1-3}$alkyl), —$OCF_3$, —$S(O)_m(C_{1-2}$alkyl), and/or —$NH_2$; and/or
(ii) —$CH_2A_1$, —$OA_1$, —$OCH_2A_1$, —$CH_2OA_1$, and/or —$CH_2SO_2A_1$, wherein $A_1$ is phenyl, pyridinyl, thiazolyl, or imidazolyl substituted with zero to 2 substituents independently selected from F, Cl, —$NH_2$, $C_{1-3}$alkyl, —$CF_3$, and/or $C_{1-2}$alkoxy;
$L_1$ is:
 (a) —$(CR_bR_b)_{2-4}$—,
 (b) —$(CH_2)_{0-2}$—$CR_c$=$CR_c$—$(CH_2)_{0-2}$, or
 (c) —$(CH_2)_{0-2}O(CH_2)_{1-2}$—;
$L_2$ is:
 (a) a bond,
 (b) —$(CR_bR_b)_{1-4}$—,
 (c) —$(CH_2)_{0-2}$—$CR_c$=$CR_c$—$(CH_2)_{0-2}$, or
 (d) —$(CH_2)_{0-2}O(CH_2)_{1-2}$—;
Q is phenyl or 5- to 6-membered heteroaryl substituted with zero to 3 substituents independently selected from F, Cl, $C_{1-3}$alkyl, —$CN$, —$NO_2$, —$NH_2$, —$CF_3$, $C_{1-2}$alkoxy, and/or —$OCF_3$;
each $R_a$ is independently F, Cl, and/or —$CH_3$; and/or two $R_a$ attached to the same carbon atom form =O;
each $R_b$ is independently H, —$CH_3$, F, —OH, and/or $C_{1-2}$alkoxy, provided that if one $R_b$ is —OH, then the second $R_b$ attached to the same carbon is not —OH or F; and
each $R_c$ is independently H, F, and/or —$CH_3$.

One embodiment provides a compound of Formula (I) or stereoisomers, N-oxides, salts, or prodrugs thereof, wherein:
Ring A is phenyl, a 5-membered heteroaryl having at least one S heteroatom, or a 6-membered heteroaryl having at least one N heteroatom;
(i) $R_1$ and $R_2$ are independently $C_{1-2}$alkyl; or
(ii) $R_1$ and $R_2$ together with the carbon atom to which they are attached, form a $C_{3-7}$cycloalkyl substituted with zero to 3 $R_a$;
each $R_3$ is independently:
(i) F, Cl, $C_{1-4}$alkyl, —$CF_3$, —$O(C_{1-2}$alkyl), —$OCF_3$, and/or —$NH_2$; and/or
(ii) —$CH_2A_1$, —$OA_1$, —$OCH_2A_1$, —$CH_2OA_1$, and/or —$CH_2SO_2A_1$, wherein $A_1$ is phenyl, pyridinyl, thiazolyl, or imidazolyl substituted with zero to 2 substituents independently selected from F, Cl, —NH$_2$, C$_{1-2}$alkyl, —CF$_3$, and/or —OCH$_3$;

L$_1$ is:
(a) —(CR$_b$R$_b$)$_{2-4}$—, or
(b) —(CH$_2$)$_{0-2}$O(CH$_2$)$_{1-2}$—;

L$_2$ is:
(a) a bond,
(b) —(CR$_b$R$_b$)$_{1-4}$—, or
(c) —(CH$_2$)$_{0-2}$O(CH$_2$)$_{1-2}$—;

Q is phenyl or 5- to 6-membered heteroaryl substituted with zero to 3 substituents independently selected from F, Cl, C$_{1-2}$alkyl, —CN, —NH$_2$, —CF$_3$, —OCH$_3$, and/or —OCF$_3$;

each R$_a$ is independently F, Cl, and/or —CH$_3$; and/or two R$_a$ attached to the same carbon atom form =O; and each R$_b$ is independently H, —CH$_3$, and/or —OH, provided that if one R$_b$ is —OH, then the second R$_b$ attached to the same carbon is not —OH or F.

One embodiment provides a compound of Formula (I) or stereoisomers, N-oxides, salts, or prodrugs thereof, wherein:
Ring A is phenyl, thiophenyl, thiazolyl, pyridinyl, or pyridinonyl;
(i) R$_1$ and R$_2$ are —CH$_3$; or
(ii) R$_1$ and R$_2$ together with the carbon atom to which they are attached, form a C$_{4-6}$cycloalkyl substituted with zero to 2 R$_a$;

each R$_3$ is independently:
(i) F, Cl, C$_{1-4}$alkyl, —CF$_3$, —OCH$_3$, —OCF$_3$, and/or —NH$_2$; and/or
(ii) —CH$_2$A$_1$, —OA$_1$, —OCH$_2$A$_1$, —CH$_2$OA$_1$, and/or —CH$_2$SO$_2$A$_1$, wherein A$_1$ is phenyl, pyridinyl, thiazolyl, or imidazolyl substituted with zero to 2 substituents independently selected from F, Cl, —NH$_2$, C$_{1-2}$alkyl, —CF$_3$, and/or —OCH$_3$;

L$_1$ is —(CR$_b$R$_b$)$_{2-4}$—;
L$_2$ is a bond or —(CR$_b$R$_b$)$_{1-4}$—;
Q is phenyl substituted with zero to 3 substituents independently selected from F, Cl, —CH$_3$, —CN, and/or —CF$_3$;

each R$_a$ is independently F and/or —CH$_3$; and/or two R$_a$ attached to the same carbon atom form =O; and each R$_b$ is independently H, —CH$_3$, and/or —OH, provided that if one R$_b$ is —OH, then the second R$_b$ attached to the same carbon is not —OH or F.

One embodiment provides a compound of Formula (I) or stereoisomers, N-oxides, salts, or prodrugs thereof, wherein said compound has the structure of Formula (II):

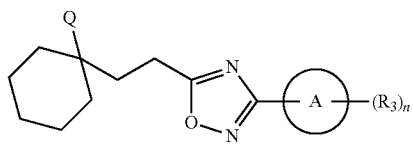

wherein:
Q is phenyl substituted with zero to 2 F;
Ring A is phenyl, thiophenyl, thiazolyl, pyridinyl, or pyridinonyl;
each R$_3$ is independently selected from:
(i) F, Cl, C$_{1-4}$alkyl, —CF$_3$, —OCH$_3$, —OCF$_3$, and/or —NH$_2$; and/or
(ii) —CH$_2$(dichloroimidazolyl), —O(trifluoromethyl pyridinyl), —OCH$_2$(methylthiazolyl), —OCH$_2$(chlorothiazolyl), —OCH$_2$(phenyl), —OCH$_2$(fluorophenyl), —OCH$_2$(chlorophenyl), —OCH$_2$(dichlorophenyl), and/or —CH$_2$SO$_2$(chlorophenyl); and
n is zero, 1, or 2.

One embodiment provides a compound of Formula (I) or stereoisomers, N-oxides, salts, or prodrugs thereof, wherein said compound has the structure of Formula (II):

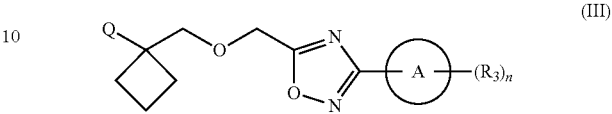

wherein:
Q is phenyl substituted with zero to 1 Cl; Ring A is phenyl;
each R$_3$ is independently selected from F, Cl, C$_{1-4}$alkyl, —CF$_3$, —OCH$_3$, —OCF$_3$, and/or —NH$_2$; and
n is zero, 1, or 2.

One embodiment provides a compound of Formula (I) or stereoisomers, N-oxides, salts, or prodrugs thereof; wherein said compound is selected from: 3-(5-(2-(1-(3,5-difluorophenyl)cyclohexyl)ethyl)-1,2,4-oxadiazol-3-yl)-6-methyl-2 (1H)-pyridinone (1); 4-(5-(2-(1-(3,5-difluorophenyl)cyclohexyl)ethyl)-1,2,4-oxadiazol-3-yl)-2(1H)-pyridinone (2); 3-(3-fluoro-4-methylphenyl)-5-(2-(1-phenylcyclohexyl)ethyl)-1,2,4-oxadiazole (3); 3-(3,5-bis(trifluoromethyl)phenyl)-5-(2-(1-phenylcyclohexyl)ethyl)-1,2,4-oxadiazole (4); 3-(4-fluorophenyl)-5-(2-(1-phenylcyclohexyl)ethyl)-1,2,4-oxadiazole (5); 3-(4-methylphenyl)-5-(2-(1-phenylcyclohexyl)ethyl)-1,2,4-oxadiazole (6); 3-phenyl-5-(2-(1-phenylcyclohexyl)ethyl)-1,2,4-oxadiazole (7); 5-(2-(1-phenylcyclohexyl)ethyl)-3-(3-(trifluoromethyl)phenyl)-1,2,4-oxadiazole (8); 3-(3-methylphenyl)-5-(2-(1-phenylcyclohexyl)ethyl)-1,2,4-oxadiazole (9); 3-(4-chlorophenyl)-5-(2-(1-phenylcyclohexyl)ethyl)-1,2,4-oxadiazol (10); 5-(2-(1-phenylcyclohexyl)ethyl)-3-(4-(trifluoromethyl)phenyl)-1,2,4-oxadiazole (11); 3-(3,4-difluorophenyl)-5-(2-(1-phenylcyclohexyl)ethyl)-1,2,4-oxadiazole (12); 3-(3-fluoro-4-(trifluoromethyl)phenyl)-5-(2-(1-phenylcyclohexyl)ethyl)-1,2,4-oxadiazole (13); 3-(4-methoxyphenyl)-5-(2-(1-phenylcyclohexyl)ethyl)-1,2,4-oxadiazole (14); 3-(4-tert-butylphenyl)-5-(2-(1-phenylcyclohexyl)ethyl)-1,2,4-oxadiazole (15); 5-(2-(1-phenylcyclohexyl)ethyl)-3-(4-(trifluoromethoxy)phenyl)-1,2,4-oxadiazole (16); 3-(2,4-dichlorophenyl)-5-(2-(1-phenylcyclohexyl)ethyl)-1,2,4-oxadiazole (17); 3-(4-(benzyloxy)phenyl)-5-(2-(1-phenylcyclohexyl)ethyl)-1,2,4-oxadiazole (18); 3-(3,5-dimethoxyphenyl)-5-(2-(1-phenylcyclohexyl)ethyl)-1,2,4-oxadiazole (19); 3-(4-((2-fluorobenzyl)oxy)phenyl)-5-(2-(1-phenylcyclohexyl)ethyl)-1,2,4-oxadiazole (20); 3-(3-(((4-chlorophenyl)sulfonyl)methyl)phenyl)-5-(2-(1-phenylcyclohexyl)ethyl)-1,2,4-oxadiazole (21); 3-(4-((2-methyl-1,3-thiazol-4-yl)methoxy)phenyl)-5-(2-(1-phenylcyclohexyl)ethyl)-1,2,4-oxadiazole (22); 3-(4-((2-chloro-1,3-thiazol-5-yl)methoxy)phenyl)-5-(2-(1-phenylcyclohexyl)ethyl)-1,2,4-oxadiazole (23); 3-(3-((4,5-dichloro-1H-imidazol-1-yl)methyl)phenyl)-5-(2-(1-phenylcyclohexyl)ethyl)-1,2,4-oxadiazole (24); 3-(4-((2,4-dichlorobenzyl)oxy)phenyl)-5-(2-(1-phenylcyclohexyl)ethyl)-1,2,4-oxadiazole (25); 3-(2,5-dimethoxyphenyl)-5-(2-(1-phenylcyclohexyl)ethyl)-1,2,4-oxadiazole (26); 3-(4-((4-chlorobenzyl)oxy)phenyl)-5-(2-(1-phenylcyclohexyl)ethyl)-1,2,4-oxadiazole (27); 3-(2,4-difluorophenyl)-5-(2-(1-phenylcyclohexyl)ethyl)-1,2,4-oxadiazole (28); 4-(5-(2-(1-phenylcyclohexyl)ethyl)-1,2,4-oxadiazol-3-yl)-2-pyridinamine (29); 2-(5-(2-(1-phenylcyclohexyl)ethyl)-1,2, 4-oxadiazol-3-yl)pyridine (30); 3-(5-chloro-2-methylphenyl)-5-(2-(1-phenylcyclohexyl)ethyl)-1,2,4-oxadiazole (31): 2-chloro-4-(5-(2-(1-phenylcyclohexyl)ethyl)-1,2,4-oxadiazol-3-yl)pyridine (32): 3-(5-(2-(1-phenylcyclohexyl)ethyl)-1,2,4-oxadiazol-3-yl)-2-pyridinamine (33); 4-(5-(2-(1-phenylcyclohexyl)ethyl)-1,2,4-oxadiazol-3-yl)pyridine 1-oxide (34); 3-(2-methyl-1,3-thiazol-4-yl)-5-(2-(1-phenylcyclohexyl)ethyl)-1,2,4-oxadiazole (35); 2-(4-(5-(2-(1-phenylcyclohexyl)ethyl)-1,2,4-oxadiazol-3-yl)phenoxy)-5-(trifluoromethyl)pyridine (36); 4-(5-(2-(1-phenylcyclohexyl)ethyl)-1,2,4-oxadiazol-3-yl)pyridine (37); 3-(5-(2-(1-phenylcyclohexyl)ethyl)-1,2,4-oxadiazol-3-yl)pyridine (89); 3-methyl-2-(5-(2-(1-phenylcyclohexyl)ethyl)-1,2,4-oxadiazol-3-yl)pyridine (39); 3-(3-methyl-2-thienyl)-5-(2-(1-phenylcyclohexyl)ethyl)-1,2,4-oxadiazole (40); and 3-(2-chloro-4-methylphenyl)-5-(((1-(4-chlorophenyl)cyclobutyl)methoxy)methyl)-1,2,4-oxadiazole (41).

The compounds of Formula (I) have GTPγS S1P$_1$ EC$_{50}$ values of 15 µM or less as measured by the S1P$_1$ Receptor GTPγS Binding Assay described herein below. Preferably, the compounds of Formula (I) have GTPγS S1P$_1$ EC$_{50}$ values in the range of 0.1 nM to 5 µM, and more preferably, in the range of from 0.1 nM to 1 µM. Other preferred compounds of Formula (I) have GTPγS S1P$_1$ EC$_{50}$ values in the range of from 0.1 nM to 100 nM.

In one embodiment, the compounds of Formula (I) are selective for S1P$_1$ activity over S1P$_3$ activity as measured by the selectivity ratio of the GTPγS S1P$_3$ EC$_{50}$ value to the GTPγS S1P$_1$ EC$_{50}$ value. The S1P$_1$ Receptor GTPγS Binding Assay and the S1P$_3$ Binding Assay are described herein below. The compounds of Formula (I) have selectivity ratios (GTPγS S1P$_3$/S1P$_1$) of at least 3.5 or greater, preferably at least 50 or greater, and more preferably at least 100 or greater. For example, suitable compounds of Formula (I) can have selectivity ratios in the range of from 50 to 50,000. Other suitable compounds of Formula (I) can have selectivity ratios in the range of from 100 to 50,000.

Definitions

The features and advantages of the invention may be more readily understood by those of ordinary skill in the art upon reading the following detailed description. It is to be appreciated that certain features of the invention that are, for clarity reasons, described above and below in the context of separate embodiments, may also be combined to form a single embodiment. Conversely, various features of the invention that are, for brevity reasons, described in the context of a single embodiment, may also be combined so as to form sub-combinations thereof. Embodiments identified herein as exemplary or preferred are intended to be illustrative and not limiting.

Unless specifically stated otherwise herein, references made in the singular may also include the plural. For example, "a" and "an" may refer to either one, or one or more.

Unless otherwise indicated, any heteroatom with unsatisfied valences is assumed to have hydrogen atoms sufficient to satisfy the valences.

The definitions set forth herein take precedence over definitions set forth in any patent, patent application, and/or patent application publication incorporated herein by reference.

Listed below are definitions of various terms used to describe the present invention. These definitions apply to the terms as they are used throughout the specification (unless they are otherwise limited in specific instances) either individually or as part of a larger group.

Throughout the specification, groups and substituents thereof may be chosen by one skilled in the field to provide stable moieties and compounds.

In accordance with a convention used in the art,

is used in structural formulas herein to depict the bond that is the point of attachment of the moiety or substituent to the core or backbone structure.

The terms "halo" and "halogen," as used herein, refer to F, Cl, Br, and I.

The term "alkyl" as used herein, refers to both branched and straight-chain saturated aliphatic hydrocarbon groups containing, for example, from 1 to 12 carbon atoms, from 1 to 6 carbon atoms, and from 1 to 4 carbon atoms. Examples of alkyl groups include, but are not limited to, methyl (Me), ethyl (Et), propyl (e.g., n-propyl and i-propyl), butyl (e.g., n-butyl, i-butyl, sec-butyl, and t-butyl), and pentyl (e.g., n-pentyl, isopentyl, neopentyl), n-hexyl, 2-methylpentyl, 2-ethylbutyl, 3-methylpentyl, and 4-methylpentyl. When numbers appear in a subscript after the symbol "C", the subscript defines with more specificity the number of carbon atoms that a particular group may contain. For example, "C$_{1-6}$alkyl" denotes straight and branched chain alkyl groups with one to six carbon atoms.

As used herein, "alkylene" refers to a bivalent alkyl radical having the general formula —(CH$_2$)$_n$—, where n is 1 to 10. Non-limiting examples include methylene, dimethylene, trimethylene, tetramethylene, pentamethylene, and hexamethylene. For example, "C$_{1-6}$alkylene" denotes straight and branched chain alkylene groups with one to six carbon atoms. Further, for example, "C$_{0-4}$ alkylene" denotes a bond and straight and branched chain alkylene groups with one to four carbon atoms.

The term "haloalkyl," as used herein, refers to an alkyl group in which one or more hydrogen atoms are replaced by halogen atom(s), the number of which can range from one up to the total number of hydrogen atoms that could otherwise exist in the parent alkyl group. Representative examples of haloalkyl groups include, but are not limited to, chloromethyl (—CH$_2$Cl), trifluoromethyl (—CF$_3$—, and 2,2,2-trifluoroethyl (—CH$_2$CF$_3$). When numbers appear in a subscript after the symbol "C", the subscript defines with more specificity the number of carbon atoms that a particular haloalkyl group may contain. For example, "C$_{1-4}$haloalkyl" denotes straight and branched chain haloalkyl groups with one to four carbon atoms.

The term "fluoroalkyl" as used herein is intended to include both branched and straight-chain saturated aliphatic hydrocarbon groups substituted with one or more fluorine atoms. For example, "C$_{1-4}$fluoroalkyl" is intended to include C1, C2, C3, and C4 alkyl groups substituted with one or more fluorine atoms. Representative examples of fluoroalkyl groups include, but are not limited to, —CF$_3$ and —CH$_2$CF$_3$.

The term "chloroalkyl" as used herein is intended to include both branched and straight-chain saturated aliphatic hydrocarbon groups substituted with one or more chlorine atoms. For example, "C$_{1-4}$ chloroalkyl" is intended to include C$_1$, C$_2$, C$_3$, and C$_4$ alkyl groups substituted with one or more chlorine atoms. Representative examples of chloroalkyl groups include, but are not limited to, —CCl$_3$ and —CH$_2$CCl$_3$.

The term "hydroxyalkyl" includes both branched and straight-chain saturated alkyl groups substituted with one or more hydroxyl groups. For example, "hydroxyalkyl" includes —CH$_2$OH, —CH$_2$CH$_2$OH, and C$_{1-4}$hydroxyalkyl.

The term "cyano" refers to the group —CN.

The term "cycloalkyl," as used herein, refers to a group derived from a non-aromatic monocyclic or polycyclic hydrocarbon molecule by removal of one hydrogen atom from a saturated ring carbon atom. Representative examples of cycloalkyl groups include, but are not limited to, cyclopropyl, cyclopentyl, and cyclohexyl. When numbers appear in a subscript after the symbol "C", the subscript defines with more specificity the number of carbon atoms that a particular cycloalkyl group may contain. For example, "C$_{3-6}$cycloalkyl" denotes cycloalkyl groups with three to six carbon atoms.

The term "alkenyl" refers to a straight or branched chain hydrocarbon radical containing from 2 to 12 carbon atoms and at least one carbon-carbon double bond. Exemplary such groups include ethenyl or allyl. For example, "C$_{2-6}$alkenyl" denotes straight and branched chain alkenyl groups with two to six carbon atoms.

The term "alkynyl" refers to a straight or branched chain hydrocarbon radical containing from 2 to 12 carbon atoms and at least one carbon to carbon triple bond. Exemplary such groups include ethynyl. For example, "C$_{2-6}$alkynyl" denotes straight and branched chain alkynyl groups with two to six carbon atoms.

The term "alkoxy," as used herein, refers to an alkyl group attached to the parent molecular moiety through an oxygen atom, for example, methoxy group (—OCH$_3$).

"Fluoroalkoxy" and "—O(fluoroalkyl)" represent a fluoroalkyl group as defined above attached through an oxygen linkage (—O—). For example, "C$_{1-4}$fluoroalkoxy" is intended to include C1, C2, C3, and C4 fluoroalkoxy groups.

The term "alkoxyalkyl" as used herein, refers to an alkoxy group attached through an alkylene group.

The term "fluoroalkoxyalkyl" as used herein, refers to a fluoroalkoxy group attached through an alkylene group.

The term "aryl," as used herein, refers to a group of atoms derived from a molecule containing aromatic ring(s) by removing one hydrogen that is bonded to the aromatic ring(s). Representative examples of aryl groups include, but are not limited to, phenyl, naphthyl, indanyl, indenyl, and 1,2,3,4-tetrahydronaphth-5-yl.

The term "benzyl," as used herein, refers to a methyl group in which one of the hydrogen atoms is replaced by a phenyl group.

The term "heteroatom" refers to oxygen (O), sulfur (S), and nitrogen (N).

The term "heterocyclo" or "heterocyclyl" may be used interchangeably and refer to non-aromatic 3- to 7-membered monocyclic groups and 6- to 11-membered bicyclic groups, in which at least one of the rings has at least one heteroatom (O, S or N), said heteroatom containing ring preferably having 1 to 3 heteroatoms independently selected from O, S, and/or N. Each ring of such a group containing a heteroatom can contain one or two oxygen or sulfur atoms and/or from one to four nitrogen atoms provided that the total number of heteroatoms in each ring is four or less, and further provided that the ring contains at least one carbon atom. The nitrogen and sulfur atoms may optionally be oxidized and the nitrogen atoms may optionally be quaternized. The fused rings completing the bicyclic group may contain only carbon atoms and may be saturated, partially saturated, or unsaturated. The heterocyclo group may be attached at any available nitrogen or carbon atom. The heterocyclo ring may be unsubstituted or may contain one or more substituents as valence allows.

Exemplary monocyclic heterocyclyl groups include oxetanyl, azetidinyl, pyrrolidinyl, imidazolinyl, oxazolidinyl, isoxazolinyl, thiazolidinyl, isothiazolidinyl, tetrahydrofuranyl, piperidinyl, piperazinyl, 2-oxopiperazinyl, 2-oxopiperidinyl, 2-oxopyrrolodinyl, 2-oxoazepinyl, azepinyl, 4-piperidonyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl. Exemplary bicyclic heterocyclo groups include quinuclidinyl.

The term "heteroaryl" refers to substituted and unsubstituted aromatic 5- or 6-membered monocyclic groups and 9- or 10-membered bicyclic groups which have at least one heteroatom (O, S or N) in at least one of the rings, said heteroatom-containing ring preferably having 1, 2, or 3 heteroatoms independently selected from O, S, and/or N. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic group may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. The heteroaryl ring system may be unsubstituted or may contain one or more substituents.

Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thiophenyl, oxadiazolyl, pyridinyl, pyrazinyl, pyrimidinyl, pyridazinyl, and triazinyl.

Exemplary bicyclic heteroaryl groups include indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridyl, dihydroisoindolyl, and tetrahydroquinolinyl.

The term "heterocyclylalkyl," as used herein, refers to an heterocyclyl group, as defined herein, appended to the parent molecular moiety through an alkylene group, as defined herein.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; and alkali or organic salts of acidic residues such as carboxylic acids. The pharmaceutically acceptable salts include the conventional non-toxic salts or the quaternary ammonium salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th Edition, p. 1418, Mack Publishing Company, Easton, Pa. (1985), the disclosure of which is hereby incorporated by reference.

Salt(s) of the Formula (I) compounds can be formed by, for example, reacting a Formula (I) compound with, for example, an equivalent amount of acid or base in a medium that allows the newly formed salt to, for example, either be precipitated out, or be isolated via lyophilization. Exemplary acidic salt(s) that the compounds of Formula (I) can form with inorganic and/or organic acids include, but are not limited to, for example, include acetate, ascorbate, benzoate, benzenesulfonate, bisulfate, bitartrate, acid citrate, citrate, ethanesulfonate, formate, fumarate, gentisinate, gluconate, glucaronate, glutamate, hydrochloride, hydrobromide, hydroiodide, isonicotinate, maleate, mesylate, methanesulfonate, nitrate, pantothenate, phosphate, acid phosphate, saccharate, salicylate, succinate, sulfate, tartrate, p-toluenesulfonate, trifluoroacetate, lactate, and pamoate [i.e., 1,1'-methylene-bis-(2-hydroxy-3-naphthoate)] salts. Such salts can be formed in accordance with methods known to a person of ordinary skill in the art.

Exemplary basic salt(s) that the compounds of Formula (I) can form with inorganic and/or organic bases include, but are not limited to, for example, ammonium salts; alkali metal salts, such as, for example, sodium, lithium and potassium salts: alkaline earth metal salts, such as, for example, calcium and magnesium salts; salts formed with organic bases, such as, for example, benzathines, dicyclohexylamines, 2-amino-2-(hydroxymethyl)propane-1,3-diol (trisamine or tris), hydrabamines (such as, for example, N,N-bis(dehydroabietyl)ethylenediamine), N-methyl-D-glucamines, N-methyl-D-glycamides, and t-butyl amines; salts formed with amino acids, such as, for example, arginine and lysine; and salts formed by using agents, such as, for example, lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), and aralkyl halides (e.g., benzyl and phenethyl bromides) to quaternize basic nitrogen-containing groups. Such salts can be formed in accordance with methods known to a person of ordinary skill in the art.

In addition, compounds of Formula (I) are, subsequent to their preparation, preferably isolated and purified to obtain a composition containing an amount by weight equal to or greater than 99% of a compound of Formula (I) ("substantially pure"), which is then used or formulated as described herein. Such "substantially pure" compounds of Formula (I) are also contemplated herein as part of the present invention.

Any compound that can be converted in vivo to provide the bioactive agent (i.e., the compound of Formula (I)) is a prodrug within the scope and spirit of the invention.

The term "prodrugs" as employed herein includes esters and carbonates formed by reacting one or more hydroxyls of compounds of Formula (I) with alkyl, alkoxy, or aryl substituted acylating agents employing procedures known to those skilled in the art to generate acetates, pivalates, methylcarbonates, benzoates, and the like.

Various forms of prodrugs are well known in the art and are described in:

a) Wermuth, C. G. et al., *The Practice of Medicinal Chemistry*, Chapter 31, Academic Press (1996);

b) Bundgaard, H. ed., *Design of Prodrugs*, Elsevier (1985);

c) Bundgaard, H., Chapter 5, "Design and Application of Prodrugs," *A Textbook of Drug Design and Development*, pp. 113-191, Krosgaard-Larsen, P. et al., eds., Harwood Academic Publishers (1991); and d) Testa, B. et al., *Hydrolysis in Drug and Prodrug Metabolism*, Wiley-VCH (2003).

In addition, compounds of the Formula (I) are, subsequent to their preparation, preferably isolated and purified to obtain a composition containing an amount by weight equal to or greater than 99% Formula (I) compound ("substantially pure" compound I), which is then used or formulated as described herein. Such "substantially pure" compounds of the Formula (I) are also contemplated herein as part of the present invention.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of a compound of the present invention alone or an amount of the combination of compounds claimed or an amount of a compound of the present invention in combination with other active ingredients effective to act as an agonist to S1P1, or effective to treat or prevent vascular disease or autoimmune diseases.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

Compounds of the present invention may contain one or more additional asymmetric carbon atoms and therefore exist in two or more stereoisomeric forms. The present invention includes all of the possible individual stereoisomers, the individual tautomeric forms thereof, together with mixtures thereof. Separation of diastereoisomers may be achieved by conventional techniques, e.g., by fractional crystallization, chromatography or HPLC of a stereoisomeric mixture of a compound of the present invention, or a suitable salt or derivative thereof. An individual enantiomer of the compound may also be prepared from a corresponding optically pure intermediate or by resolution, such as by HPLC of the corresponding racemate using a suitable chiral support or by fractional crystallization of the diastereoisomeric salts formed by reaction of the corresponding racemate with a suitable optically active acid or base, as appropriate. All stereoisomers of the compounds of the instant invention are contemplated, either in admixture or in pure or substantially pure form.

The compounds of the present invention are intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

Also embraced within this invention is a class of pharmaceutical compositions comprising the compound of Formula (I) or a pharmaceutically acceptable salt thereof in association with one or more non-toxic, pharmaceutically-acceptable carriers and/or diluents and/or adjuvants (collectively referred to herein as "carrier" materials) and, if desired, other active ingredients. The compounds of Formula (I) may be administered by any suitable route, preferably in the form of a pharmaceutical composition adapted to such a route, and in a dose effective for the treatment intended. The compounds and compositions of the present invention may, for example, be administered orally, mucosally, or parentally including intravascularly, intravenously, intraperitoneally, subcutaneously, intramuscularly intrasternally and infusion techniques, in dosage unit formulations containing conventional pharmaceutically acceptable carriers, adjuvants, and vehicles. For example, the pharmaceutical carrier may contain a mixture of mannitol or lactose and microcrystalline cellulose. The mixture may contain additional components such as a lubricating agent, e.g., magnesium stearate and a disintegrating agent such as crospovidone. The carrier mixture may be filled into a gelatin capsule or compressed as a tablet.

The pharmaceutically active compounds of this invention can be processed in accordance with conventional methods of pharmacy to produce medicinal agents for administration to patients, including humans and other mammals.

For oral administration, the pharmaceutical composition may be in the form of, for example, a tablet, capsule, suspension, or liquid. The pharmaceutical composition is preferably made in the form of a dosage unit containing a particular amount of the active ingredient. Examples of such dosage units are tablets or capsules. For example, these may contain an amount of active ingredient from about 0.5 to 2000 mg, preferably from about 0.5 to 500 mg, more preferably from about 0.5 to 150 mg. A suitable daily dose for a human or other mammal may vary widely depending on the condition of the patient and other factors, but, once again, can be determined using routine methods.

The amounts of compounds that are administered and the dosage regimen for treating a disease condition with the compounds and/or compositions of this invention depends on a variety of factors, including the age, weight, sex, the medical condition of the subject, the type of disease, the severity of the disease, the route and frequency of administration, and the particular compound employed. Thus, the dosage regimen may vary widely, but can be determined routinely using standard methods. A daily dose of about 0.01 to 1500 mg/kg body weight, preferably between about 0.5 and about 50 mg/kg body weight and most preferably between about 0.1 to 20 mg/kg body weight, may be appropriate. The daily dose can be administered in one to four doses per day.

For therapeutic purposes, the active compounds of this invention are ordinarily combined with one or more adjuvants appropriate to the indicated route of administration. If administered orally, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinyl alcohol, and/or polyvinylpyrrolidone, and then tableted or encapsulated for convenient administration. Such capsules or tablets may contain a controlled-release formulation as may be provided in a dispersion of active compound in hydroxypropylmethyl cellulose.

The oily phase of the emulsions comprising compounds of Formula (I) may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. Emulsifiers and emulsion stabilizers suitable for use in the formulation of the present invention include Tween 60, Span 80, cetostearyl alcohol, myristyl alcohol, glyceryl monostearate, sodium lauryl sulfate, glyceryl distearate alone or with a wax, or other materials well known in the art.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (i.e., CAPTISOL®), cosolvent solubilization (i.e., propylene glycol) or micellar solubilization (i.e., Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

The pharmaceutical compositions may be subjected to conventional pharmaceutical operations such as sterilization and/or may contain conventional adjuvants, such as preservatives, stabilizers, wetting agents, emulsifiers, and buffers.

Tablets and pills can additionally be prepared with enteric coatings. Such compositions may also comprise adjuvants, such as wetting, sweetening, flavoring, and perfuming agents.

Pharmaceutical compositions of this invention comprise the compound of Formula (I), or a pharmaceutically acceptable salt thereof, and optionally an additional agent selected from any pharmaceutically acceptable carrier, adjuvant, and vehicle. Alternate compositions of this invention comprise a compound of the Formula (I) described herein, or a pharmaceutically acceptable salt thereof, and a pharmaceutically acceptable carrier, adjuvant, or vehicle.

Pharmaceutically acceptable carriers, adjuvants, and vehicles that may be used in the pharmaceutical compositions of this invention include, but are not limited to, ion exchangers, alumina, aluminum stearate, lecithin, self-emulsifying drug delivery systems (SEDDS) such as d-alpha-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as alpha-, beta-, and gamma-cyclodextrin, or chemically modified derivatives such as hydroxyalkylcyclodextrins, including 2- and 3-hydroxypropyl-cyclodextrins, or other solubilized derivatives may also be advantageously used to enhance delivery of compounds of the formulae described herein.

Utility

The human immune system has evolved to defend the body from micro-organisms, viruses, and parasites that can cause infection, disease or death. Complex regulatory mechanisms ensure that the various cellular components of the immune system target the foreign substances or organisms, while not causing permanent or significant damage to the individual. While the initiating events are not well understood at this time, in autoimmune disease states the immune system directs its inflammatory response to target organs in the afflicted individual. Different autoimmune diseases are typically characterized by the predominate or initial target organ or tissues affected; such as the joint in the case of rheumatoid arthritis, the thyroid gland in the case of Hashimoto's thyroiditis, the central nervous system in the case of multiple sclerosis, the pancreas in the case of type I diabetes, and the bowel in the case of inflammatory bowel disease. Thus it has been observed that therapeutic agents which act on the immune system or certain cell types of the immune system (such as B-lymphocytes, and T lymphocytes, T cells) may have utility in more than one autoimmune disease.

It is well recognized in the art, including the literature references cited herein, that S1P receptors are good targets for a wide variety of therapeutic applications, including autoimmune diseases. S1P receptors make good drug targets, because individual receptors are both tissue- and response-specific. Tissue specificity of the S1P receptors is important, because development of an agonist or antagonist selective for one receptor localizes the cellular response to tissues containing that receptor, limiting unwanted side effects. Response specificity of the S1P receptors is also important because it allows for development of agonists or antagonists that initiate or suppress certain cellular responses without affecting other processes. Therefore, compounds that act on some S1P receptor family members while having diminished or no activity at other family members are desirable and are expected to provide a therapeutic effect with an improved side effect profile (i.e., reduction or elimination of unwanted side effects).

As used herein, the term "agonist" in reference to $S1P_1$ refers to an agent which exerts pharmacological effects such as decreased motility of T cells, decreased trafficking of T cells, or decreased egress of T cells from lymphoid tissues. (Rosen et al., *Trends in Immunology*, 28:102 (2007)).

By virtue of their $S1P_1$ activity as agonists, the compounds of the present invention are immunoregulatory agents useful for treating or preventing autoimmune or chronic inflammatory diseases. The compounds of the present invention are useful to suppress the immune system in instances where immunosuppression is in order, such as in bone marrow, organ or transplant rejection, autoimmune and chronic inflammatory diseases, including systemic lupus erythematosis, chronic rheumatoid arthritis, type I diabetes mellitus, inflammatory bowel disease, biliary cirrhosis, uveitis, multiple sclerosis, Crohn's disease, ulcerative colitis, bullous pemphigoid, sarcoidosis, psoriasis, autoimmune myositis, Wegener's granulomatosis, ichthyosis, Graves ophthalmopathy, and asthma.

More particularly, the compounds of the present invention are useful to treat or prevent a disease or disorder selected from the group consisting of: transplantation of organs or tissue, graft-versus-host diseases brought about by transplantation, autoimmune syndromes including rheumatoid arthritis, systemic lupus erythematosus, Hashimoto's thyroiditis, multiple sclerosis, myasthenia gravis, type I diabetes, uveitis, posterior uveitis, allergic encephalomyelitis, glomerulonephritis, post-infectious autoimmune diseases including rheumatic fever and post-infectious glomerulonephritis, inflammatory and hyperproliferative skin diseases, psoriasis, psoriatic arthritis, atopic dermatitis, contact dermatitis, eczematous dermatitis, seborrheic dermatitis, lichen planus, pemphigus, bullous pemphigoid, epidermolysis bullosa, urticaria, angioedemas, vasculitis, erythema, cutaneous eosinophilia, lupus erythematosus, acne, alopecia greata, keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer, scleritis, Graves' ophthalmopathy, Vogt-Koyanagi-Harada syndrome, sarcoidosis, pollen allergies, reversible obstructive airway disease, bronchial asthma, allergic asthma, intrinsic asthma, extrinsic asthma, dust asthma, chronic or inveterate asthma, late asthma and airway hyper-responsiveness, bronchitis, gastric ulcers, vascular damage caused by ischemic diseases and thrombosis, ischemic bowel diseases, inflammatory bowel diseases, necrotizing enterocolitis, intestinal lesions associated with thermal burns, coeliac diseases, proctitis, eosinophilic gastroenteritis, mastocytosis, Crohn's disease, ulcerative colitis, migraine, rhinitis, eczema, interstitial nephritis, Goodpasture's syndrome, hemolytic-uremic syndrome, diabetic nephropathy, multiple myositis, Guillain-Barre syndrome, Meniere's disease, polyneuritis, multiple neuritis, mononeuritis, radiculopathy, hyperthyroidism, Basedow's disease, pure red cell aplasia, aplastic anemia, hypoplastic anemia, idiopathic thrombocytopenic purpura, autoimmune hemolytic anemia, agranulocytosis, pernicious anemia, megaloblastic anemia, anerythroplasia, osteoporosis, sarcoidosis, fibroid lung, idiopathic interstitial pneumonia, dermatomyositis, leukoderma vulgaris, ichthyosis vulgaris, photoallergic sensitivity, cutaneous T cell lymphoma, arteriosclerosis, atherosclerosis, aortitis syndrome, polyarteritis nodosa, myocardosis, scleroderma, Wegener's granuloma, Sjögren's syndrome, adiposis, eosinophilic fascitis, lesions of gingiva, periodontium, alveolar bone, substantia ossea dentis, glomerulonephritis, male pattern alopecia or alopecia senilis by preventing epilation or providing hair germination and/or promoting hair generation and hair growth, muscular dystrophy, pyoderma and Sezary's syndrome, Addison's disease, ischemia-reperfusion injury of organs which occurs upon preservation, transplantation or ischemic disease, endotoxin-shock, pseudomembranous colitis, colitis caused by drug or radiation, ischemic acute renal insufficiency, chronic renal insufficiency, toxinosis caused by lung-oxygen or drugs, lung cancer, pulmonary emphysema, cataracta, siderosis, retinitis pigmentosa, senile macular degeneration, vitreal scarring, corneal alkali burn, dermatitis erythema multiforme, linear IgA ballous dermatitis and cement dermatitis, gingivitis, periodontitis, sepsis, pancreatitis, diseases caused by environmental pollution, aging, carcinogenesis, metastasis of carcinoma and hypobaropathy, disease caused by histamine or leukotriene-$C_4$ release, Behcet's disease, autoimmune hepatitis, primary biliary cirrhosis, sclerosing cholangitis, partial liver resection, acute liver necrosis, necrosis caused by toxin, viral hepatitis, shock, or anoxia, B-virus hepatitis, non-A/non-B hepatitis, cirrhosis, alcoholic cirrhosis, hepatic failure, fulminant hepatic failure, late-onset hepatic failure, "acute-on-chronic" liver failure, augmentation of chemotherapeutic effect, cytomegalovirus infection, HCMV infection, AIDS, cancer, senile dementia, trauma, neuropathic pain, and chronic bacterial infection.

One embodiment provides a method for treating autoimmune and/or inflammatory diseases, comprising administering to a mammal in need thereof at least one compound of Formula (I) or a pharmaceutically acceptable salt thereof. Another embodiment provides the compounds of Formula (I) or pharmaceutically acceptable salts thereof, for use in therapy for the treatment of autoimmune and/or inflammatory diseases. In another embodiment, provided is the use of the compounds of Formula (I) or pharmaceutically acceptable salts thereof, for the manufacture of a medicament for the treatment or prophylaxis of autoimmune and/or inflammatory disease. A therapeutically effective amount may be employed in these embodiments. Preferably, in these embodiments, the autoimmune and inflammatory diseases are selected from multiple sclerosis, rheumatoid arthritis, inflammatory bowel disease (including Crohn's disease and ulcerative colitis), psoriasis, and as an agent to prevent the rejection of transplanted organs. The method of the present embodiment includes administration of a therapeutically effect amount of a compound of Formula (I) or a pharmaceutically effective salt thereof.

In another embodiment, a method for treating vascular disease is provided comprising administering to a mammal in need thereof at least one compound of Formula (I) or a pharmaceutically acceptable salt thereof. Another embodiment provides the compounds of Formula (I) or pharmaceutically acceptable salts thereof, for use in therapy for the treatment of vascular disease. In another embodiment, provided is the use of the compounds of Formula (I) or pharmaceutically acceptable salts thereof, for the manufacture of a medicament for treatment of vascular disease. A therapeutically effective amount may be employed in these embodiments. Preferably, in these embodiments, the vascular disease is selected from atherosclerosis and ischemia reperfusion injury.

The methods of treating S1P1-associated conditions may comprise administering compounds of Formula (I) alone or in combination with each other and/or other suitable therapeutic agents useful in treating such conditions. Accordingly, "therapeutically effective amount" is also intended to include an amount of the combination of compounds claimed that is effective to act as an agonist at the S1P1 receptor. The combination of compounds is preferably a synergistic combination. Synergy, as described, for example, by Chou et al., *Adv. Enzyme Regul.*, 22:27-55 (1984), occurs when the effect of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, increased efficacy, or some other beneficial effect of the combination compared with the individual components.

Exemplary of such other therapeutic agents include corticosteroids or glucocorticoids such as dexamethasone, methylprednisolone, prednisolone, and prednisone; PDE4 inhibitors such as rolipram, cilomilast, roflumilast, and oglemilast; cytokine-suppressive anti-inflammatory drugs (CSAIDs) and inhibitors of p38 kinase, 4-substituted imidazo[1,2-A]quinoxalines as disclosed in U.S. Pat. No. 4,200,750; antibodies or fusion proteins directed to cell surface molecules such as CD2, CD3, CD4, CD8, CD20 such as RITUXAN®, CD25, CD30, CD40, CD69, CD80 (B7.1), CD86 (B7.2), CD90, CTLA, for example abatacept (ORENCIA®), belatacept, or their ligands including CD154 (GP39, or CD40L); antibodies to, fusion proteins, or soluble receptors of human cytokines or growth factors, for example, TNF such as, infliximab (REMICADE®), etanercept (Embrel), adalimumab (HUMIRA®), LT, 1'-1 such as anakinra (KINERET®) (an IL-1 receptor antagonist), IL-2, IL-4, IL-5, 11-6, such as CNTO 328 (a chimeric anti-IL-6 antibody), Il-7, Il-8, Il-12, Il-15, Il-16, Il-17, Il-21, Il-23 such as Ustekinumab (a human anti-IL-12/23 monoclonal antibody), and interferons such as interferon beta 1a (AVONEX®, REBIF®), interferon beta 1b (BETASERON®); integrin receptor antagonists such as TYSABRI®; polymeric agents such as glatiramer acetate (COPAXONE®); sulfasalazine, mesalamine, hydroxychloroquine, non-steroidal anti-inflammatory drugs (NSAIDs) such as salicylates including aspirin, salsalate, and magnesium salicylate, and non-salicylates such as, ibuprofen, naproxen, meloxicam, celecoxib and rofecoxib; antiviral agents such as abacavir; antiproliferative agents such as methotrexate, mercaptopurine, leflunomide, cyclosporine, mycophenololate, FK506 (tacrolimus, PROGRAF®); cytotoxic drugs such as azathioprine and cyclophosphamide; nuclear translocation inhibitors, such as deoxyspergualin (DSG); gold containing products such as auronofin; penicillamine, and rapamycin (sirolimus or RAPAMUNE®) or derivatives thereof.

The above other therapeutic agents, when employed in combination with the compounds of the present invention, may be used, for example, in those amounts indicated in the Physicians' Desk Reference (PDR) or as otherwise determined by one of ordinary skill in the art. In the methods of the present invention, such other therapeutic agent(s) may be administered prior to, simultaneously with, or following the administration of the inventive compounds.

Methods of Preparation

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety by reference.

The compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art and alternate methods must then be used. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene et al. (*Protective Groups in Organic Synthesis*, Fourth Edition, Wiley and Sons (2006)).

Scheme I

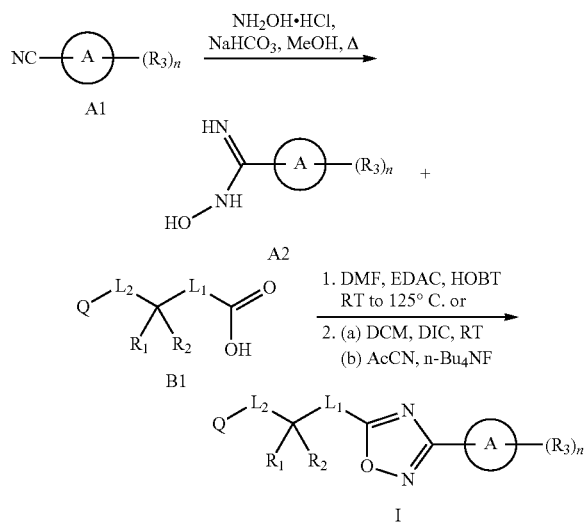

Oxadiazoles of formula I can be synthesized using the protocol outlined in Scheme I. Treatment of nitrile A1 with hydroxylamine hydrochloride in the presence of a suitable base like sodium bicarbonate yields the aldoximine intermediate A2. Reaction of intermediate A2 with carboxylic acid intermediate B1 in the presence of HOBT and EDAC in an aprotic solvent such as DMF at room temperature to 125° C. forms oxadiazole C1. Alternatively intermediate A2 can be reacted with acid intermediate B1 with DIC, followed by treatment with tetra-n-butylammonium fluoride to form I.

Scheme II

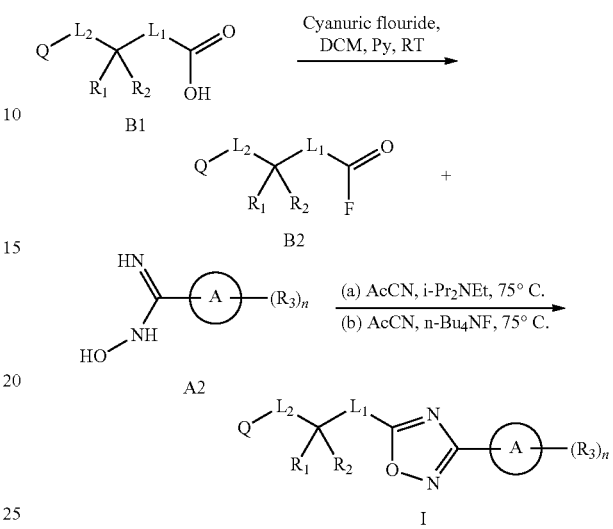

Oxadiazoles of formula I may also be synthesized using the protocol outlined in Scheme II. Carboxylic acid intermediate B1 can be converted to its acid fluoride B2 by reaction with cyanuric fluoride in presence of an organic base such as pyridine. Acid fluoride B2 in treated with aldoximine intermediate A2 in acetonitrile in the presence of an organic base such as Hunig's base and subsequently reacted with tetra-n-butylammonium fluoride to form I.

Intermediates A2 (Schemes I and II) were prepared using a general procedure as outlined below for the synthesis of Intermediate 1.

ABBREVIATIONS

Ac acetyl
AcCN acetonitrile
AcOH acetic acid
anhyd. anhydrous
aq. aqueous
9-BBN 9-borabicyclo[3.3.1]nonane
CDI carbonyldiimidazole
conc. concentrated
$BF_3.OEt_2$ boron trifluoride diethyl etherate
Bn benzyl
BOP bis(2-oxo-3-oxazolidinyl)phosphonic
Bu butyl
Boc tert-butoxycarbonyl
Cbz-N N-carbobenzyloxy
$CH_2N_2$ diazomethane
DIBAL-H diisobutylaluminum hydride
DMA N,N-dimethylacetamide
DMAP dimethylaminopyridine
DME dimethyl ether
DMF dimethylformamide
DMSO dimethylsulfoxide
EDAP ethyldilethylaminopropyl carbodiimide
EDCI 1-(3-dimethylaminopropyl)-3-ethylcarbodiimide hydrochloride
EtOAc ethyl acetate
Et ethyl EtOH ethanol
H hydrogen
h hour(s).
hrs hour(s).
i iso
HMPA hexamethylphosphoramide
HOAc acetic acid
HPLC high pressure liquid chromatography
LAH lithium aluminum hydride
LC liquid chromatography
LDA lithium diisopropylamine
m-CPBA meta-chloroperoxybenzoic acid
Me methyl
MeOH methanol
min. minute(s).
mins minute(s).
$M^{+1}$ $(M+H)^+$
MS mass spectrometry
n normal
NaHMDS sodium bis(trimethylsilyl) amide
NCS N-chlorosuccinamide
NMO N-methylmorpholine-N-oxide
2-$PCy_2$-2'6'-(O-iPr)$_2$-biphenyl 2-(dicyclohexylphosphino)-2',6'-isopropoxybiphenyl
PhCONCS benzyolyisothiocyanate
Pd/C palladium on carbon
Pd(OAc)$_2$ palladium acetate
Pd(PPh$_3$)$_4$ tetrakis(triphenylphosphine)palladium
Ph phenyl
PPh$_3$ triphenylphosphine
Pr propyl
PSI pounds per square inch
Ret Time retention time
rt or RT room temperature
sat. saturated
TBAF tetrabutylammonium fluoride
t-BuOH tertiary butyl alcohol
TEMPO 2,2,6,6-tetramethylpiperidine 1-oxyl
TFA trifluoroacetic acid
THF tetrahydrofuran
TMS trimethylsilane
TMSCN trimethylsilyl cyanide

EXAMPLES

The following examples illustrate the particular and preferred embodiments of the present invention and do not limit the scope of the present invention. Chemical abbreviations and symbols as well as scientific abbreviations and symbols have their usual and customary meanings unless otherwise specified. Additional abbreviations employed in the Examples and elsewhere in this application are defined above. Common intermediates are generally useful for the preparation of more than one Example and are identified sequentially (e.g., Intermediate 1, Intermediate 2, etc. and are abbreviated as Int. 1, Int. 2, etc. Compounds of the Examples are identified by the example and step in which they were prepared (e.g., "1-A" denotes the Example 1, step A), or by the example only where the compound is the title compound of the example (for example, "1" denotes the title compound of Example 1). In some instances alternate preparations of intermediates or examples are described. Frequently chemists skilled in the art of synthesis may devise alternative preparations which may be desirable based on one or more considerations such as shorter reaction time, less expensive starting materials, ease of operation, amenable to catalysis, avoidance of toxic reagents, accessibility of specialized instrumentation, and decreased number of linear steps. The intent of describing alternative preparations is to further enable the preparation of the examples of this invention. In some instances some functional groups in the outlined examples and claims may be replaced by well known biosteric replacements known in the art, for example, replacement of a carboxylic acid group with a tetrazole or a phosphate moiety.

Intermediate 1

5-Chloro-N'-hydroxy-2-methylbenzimidamide

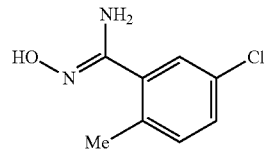

(Int. 1)

A solution of 5-chloro-2-methylbenzonitrile (1.5 g, 9.89 mmol), hydroxylamine hydrochloride (1.38 g, 19.79 mmol) and sodium bicarbonate (3.33 g, 39.6 mmol) in methanol (100 mL) was heated to 70° C. for 6 h. The mixture was cooled to room temperature and diluted with methanol (100 mL). The mixture was filtered, and the filtrate was concentrated, diluted with water and extracted with EtOAc (100 mL, 3×). The EtOAc extract was dried over MgSO$_4$, filtered and concentrated under reduced pressure to obtain crude 5-chloro-N'-hydroxy-2-methylbenzimidamide (1.8 g, 99% crude yield). LC/MS: m/e 185.0 (M+H)$^+$. $^1$H NMR (400 MHz, CD$_3$OD) δ ppm 7.30-7.29 (2 H, m), 7.23 (1 H, d), 2.36 (3H, s).

Intermediate 2

3-(1-Phenylcyclohexyl)propanoic acid

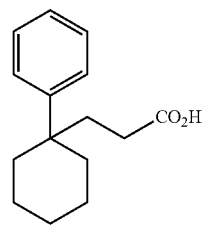

(Int. 2)

Int. 2-A: 3-(2-Oxo-1-phenylcyclohexyl)propanenitrile

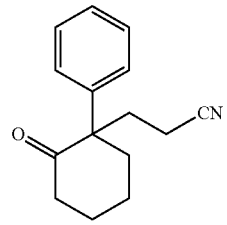

(Int. 2-A)

Reference: Bachmann, W. E. et al., *JACS*, 72:3388 (1950).
Triton B surfactant (500 μL) was added to a stirred solution of 2-phenylcyclohexanone (5 g, 28.7 mmol) in dioxane (40 mL). A solution of acrylonitrile (1.8 g, 33.9 mmol) in dioxane (5 mL) was added dropwise. A slight exotherm was observed. The solution was stirred at room temperature for 3 h and concentrated. The residue was diluted with EtOAc (50 mL) and washed with water (20 mL, 2×). The EtOAc extract was dried (MgSO$_4$), filtered, and concentrated. The residual oil was chromatographed on a silica gel column. Elution with 2% EtOAc in heptane, followed by 5% EtOAc in heptane afforded 3-(2-oxo-1-phenylcyclohexyl)propanenitrile (Int. 2-A, 5.05 g, 77% yield) as a colorless oil. HPLC: $t_R$=2.73 min, YMC Combi S5 ODS 4.6×50 mm, 4 min gradient, Detection Wave length 220 nm, Starting solvent: 10% aq. MeOH-0.2% H$_3$PO$_4$; Final solvent: 90% aq. MeOH-0.2% H$_3$PO$_4$. LC/MS: m/e 228.26 (M+H)$^+$, 250.14 (M+Na)$^+$.

Int. 2-B: 3-(2-Oxo-1-phenylcyclohexyl)propanoic acid

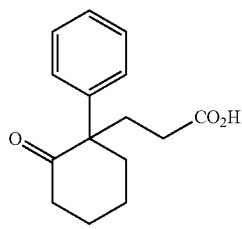

(Int. 2-B)

A mixture of 3-(2-oxo-1-phenylcyclohexyl)propanenitrile (5.05 g, 22.22 mmol) in acetic acid (11.1 mL), conc. HCl (33.2 mL), and water (11.1 mL) was refluxed for 16 h under N$_2$, cooled to room temperature, and poured into water (66 mL). The product separated out as an layer of oil. The suspension was cooled to 0° C. in an ice bath for 30 min. with occasional swirling and the crystallized product was collected by filtration and rinsed several times with water, and dried in vacuo to obtain 3-(2-oxo-1-phenylcyclohexyl)propanoic acid (Int. 2-B, 4.77 g, 85% yield) as a white crystalline solid. HPLC: $t_R$=2.47 min, YMC Combiscreen ODS-A 4.6×50 mm, 4 min gradient, Detection Wave length 220 nm, Starting solvent: 10% aq. MeOH-0.1% TFA; Final solvent: 90% aq. MeOH-0.1% TFA. LC/MS: m/e 247.2 (M+H)$^+$, 229.2 (M+H-H$_2$O)$^+$.

Int. 2: 3-(1-Phenylcyclohexyl)propanoic acid

A mixture of 3-(2-oxo-1-phenylcyclohexyl)propanoic acid (1 g, 4.06 mmol), potassium hydroxide (0.770 g, 13.72 mmol), hydrazine monohydrate (0.348 mL, 6.09 mmol), and ethylene glycol (5 mL) was heated to 130° C. for 1.5 h. The condenser was removed and the mixture was heated to 200° C. for 30 min. The reaction mixture was then heated under reflux with a reflux condenser for additional 1.5 h. The reaction mixture was cooled to room temperature and diluted with 1N HCl to a total reaction volume of 25 mL. The precipitated product was collected by filtration, washed several times with water, and dried in vacuo to obtain 3-(1-phenylcyclohexyl)propanoic acid as a white solid (Int. 2, 923 mg, 93% yield). HPLC: $t_R$=3.7 min, Chromolith SpeedRod 4.6×50 mm, 4 min gradient, Detection Wave length 220 nm, Starting solvent: 10% aq. MeOH-0.2% H$_3$PO$_4$; Final solvent: 90% aq. MeOH-0.2% H$_3$PO$_4$. LC/MS: m/e 215.19 (M+H-H$_2$O)$^+$.

Intermediate 3

3-(1-(3,4-Difluorophenyl)cyclohexyl)propanoic acid

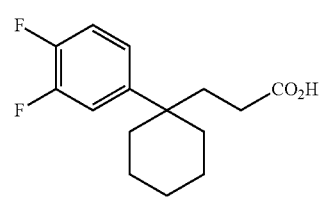

(Int. 3)

Int. 3-A: 1-(3,4-Difluorophenyl)cyclohexanecarbonitrile

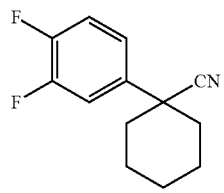

(Int. 3-A)

To a solution of 2-(3,4-difluorophenyl)acetonitrile (2 g, 13.06 mmol) in 20 mL of DMF at 0° C. was added 60% sodium hydride (1.149 g, 28 7 mmol), and the mixture was stirred at the same temperature for 5 mins. Then a solution of 1,5-dibromopentane (1.779 mL, 13.06 mmol) in 20 mL of DMF was added dropwise and the mixture was stirred at a temperature in the range of 0° C. to room temperature for 5 hrs. The reaction was quenched with water, and extracted with EtOAc. The mixture was washed with water and brine. The combined aqueous layers were back extracted with EtOAc once and washed with brine. The combined extracts were dried over Na$_2$SO$_4$ and evaporated to give an oily residue. It was purified by Combiflash (120 g silica gel) eluting with 1:9 EtOAc-hexane to give 1-(3,4-difluorophenyl)cyclohexanecarbonitrile (Int. 3-A, 2.52 g, 11.39 mmol, 87% yield). $^1$H NMR (400 MHz, CDCl$_3$) δ ppm 7.12-7.35 (3 H, m), 2.14 (2 H, d, J=11.86 Hz), 1.75-1.95 (6 H, m), 1.64-1.75 (2 H, m).

Int. 3-B: 1-(3,4-Difluorophenyl)cyclohexanecarbaldehyde

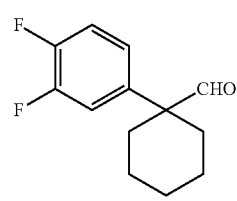

(Int. 3-B)

To a solution of 1-(3,4-difluorophenyl)cyclohexanecarbonitrile (Int. 3-A, 1 g, 4.52 mmol) in toluene (10 mL) at 0° C. was added 1M DiBAL-H (9.94 mL, 9.94 mmol) in dichloromethane, and the mixture was stirred at a temperature in the range of from 0° C. to room temperature for 5 hrs. The reaction was quenched with dropwise addition of 0.8 mL of MeOH and stirred for 5 mins. To the mixture was added 15 mL of 2N HCl slowly with stirring. After stirring for 20 mins, the product was extracted with ethyl acetate, and the extracts were washed with water and brine. It was dried over sodium sulfate and evaporated to give 1-(3,4-difluorophenyl)cyclohexanecarbaldehyde as an oil.

Int. 3-C: (E)-Ethyl 3-(1-(3,4-difluorophenyl)cyclohexyl)acrylate

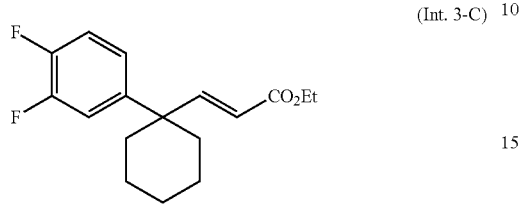

(Int. 3-C)

To a solution of triethyl phosphonoacetate (1.802 mL, 9.00 mmol) in THF (20 mL) at 0° C. was added 1M potassium t-butoxide (9.00 mL, 9.00 mmol) dropwise, and the mixture was stirred at the same temperature. After 15 mins, a solution of 1-(3,4-difluorophenyl)cyclohexanecarbaldehyde (Int. 3-B, 1.009 g, 4 5 mmol) in 10 mL of THF was added, and the mixture was stirred at room temperature for 2 hrs. The mixture was diluted with EtOAc, washed with water and brine, dried over $Na_2SO_4$, and evaporated to give an oily residue. The residue was purified by Combiflash (80 g silica gel) eluting with 5:95 EtOAc-hexane to give (E)-ethyl 3-(1-(3,4-difluorophenyl)cyclohexyl)acrylate (Int. 3-C, 608 mg, 45.9% yield for 2 steps) as an oil. $^1H$ NMR (400 MHz, $CDCl_3$) δ ppm 6.98-7.16 (3 H, m), 6.91 (1 H, d, J=15.82 Hz), 5.60 (1 H, d, J=16.26 Hz), 4.17 (2 H, q, J=7.18 Hz), 1.83-2.06 (4 H, m), 1.40-1.61 (6 H, m), 1.27 (3 H, t, J=7.03 Hz).

Int. 3-D: Ethyl 3-(1-(3,4-difluorophenyl)cyclohexyl)propanoate

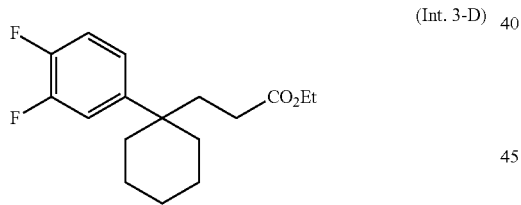

(Int. 3-D)

To a solution of (E)-ethyl 3-(1-(3,4-difluorophenyl)cyclohexyl)acrylate (Int. 3-C, 550 mg, 1.869 mmol) in MeOH (20 mL) was added ~150 mg of 10% Pd/C (wet, 50%), and the mixture was stirred under hydrogen (50 psi) for 6 hrs. The catalyst was removed by filtering through Celite and the solvent was evaporated off to give ethyl 3-(1-(3,4-difluorophenyl)cyclohexyl)propanoate as an oil. LC/MS: m/e 297.16 (M+H)$^+$.

Int. 3: 3-(1-(3,4-Difluorophenyl)cyclohexyl)propanoic acid

To a solution of ethyl 3-(1-(3,4-difluorophenyl)cyclohexyl)propanoate (Int. 3-D, 540 mg, 1.822 mmol) in MeOH (15 mL) was added 1N NaOH (3.64 mL, 3.64 mmol), and the mixture was stirred at room temperature for 20 hrs. Since the reaction was not complete on TLC, an additional 1.82 mL of 1N NaOH was added, and it was continued to stir for 3 hrs. TLC showed that the reaction was complete. Next, the reaction mixture was acidified with the addition of 6 mL of 1N HCl, and the product was extracted with EtOAc. The extract was washed with water and brine, dried over $Na_2SO_4$, and evaporated to give 3-(1-(3,4-difluorophenyl)cyclohexyl)propanoic acid (Int. 3, 489 mg, 1.822 mmol, 100% yield) as a white solid.

Intermediate 4

(E)-3-(1-(3,4-Difluorophenyl)cyclohexyl)acrylic acid

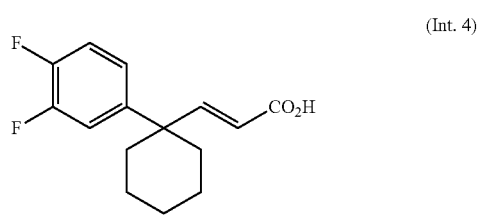 [SMILES: O=C(O)/C=C/C1(c2ccc(F)c(F)c2)CCCCC1]

(Int. 4)

To a solution of (E)-ethyl 3-(1-(3,4-difluorophenyl)cyclohexyl)acrylate (Preparation Int. 3-C, 53 mg, 0.180 mmol) in MeOH (1 mL) was added 1M NaOH (0.216 mL, 0.216 mmol), and the mixture was stirred at room temperature overnight. The mixture was acidified by the addition of 0.3 mL of 1N HCl, and the product was extracted with EtOAc. The extract was washed with brine, dried over $Na_2SO_4$ and evaporated to give the (E)-3-(1-(3,4-difluorophenyl)cyclohexyl)acrylic acid as an oil. $^1H$ NMR (400 MHz, $CDCl_3$) δ ppm 11.94 (1 H, br. s.), 7.11 (2 H, m), 7.02 (1H, d, J=15.82 Hz), 6.98-7.06 (1H, m), 5.62 (1 H, d, J=15.82 Hz), 1.83-2.06 (4 H, m), 1.37-1.65 (6 H, m).

Intermediate 5

(E)-4-(1-(4-Fluorophenyl)cyclohexyl)but-3-enoic acid

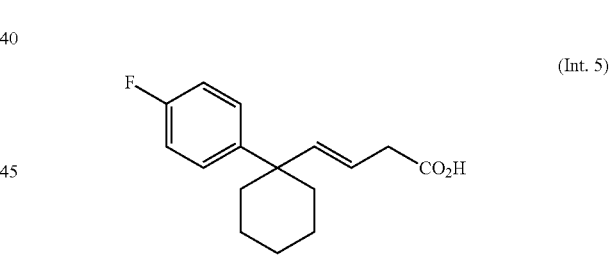

(Int. 5)

To a stirred suspension of 1-(4-fluorophenyl)cyclohexanecarbaldehyde (160 mg, 0.776 mmol) and 2-carboxyethyl triphenylphosphonium bromide (483 mg, 1.164 mmol) in THF (7 mL) at −78° C. was added 1M lithium bis(trimethylsilyl)amide (2.172 mL, 2.172 mmol) in THF dropwise, and the mixture was stirred for 30 mins at −78° C., and 30 mins at a temperatures in the range of from −78° C. to room temperature. Next, the mixture was stirred overnight at room temperature. After addition of 3 mL of 1N HCl, the mixture was extracted with EtOAc (2×), and the combined extracts were washed with brine, dried over $Na_2SO_4$ and evaporated to give an oily residue. The residue was purified by Combiflash (24 g silica gel) eluting with 5:95 followed by 3:7 EtOAc-hexane to give (E)-4-(1-(4-fluorophenyl)cyclohexyl)but-3-enoic acid (37.7 mg, 0.144 mmol, 18.53% yield) along with the unreacted starting material (41.5 mg). $^1H$ NMR (400 MHz, $CDCl_3$) δ ppm 7.28-7.33 (2 H, m), 6.93-6.99 (2 H, m), 5.97 (1

H, dt, J=11.64, 1.76 Hz), 5.58 (1 H, dt, J=11.64, 7.25 Hz), 2.59 (2 H, dd, J=7.25, 1.76 Hz), 1.86-1.96 (2 H, m), 1.54-1.76 (8 H, m), 1.22-1.33 (2 H, m).

Intermediate 6

(E)-4-(1-(4-Fluorophenyl)cyclohexyl)butanoic acid

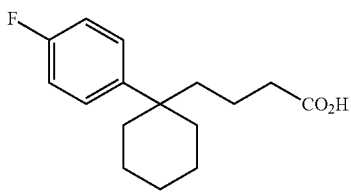
(Int. 6)

To a solution of (E)-4-(1-(4-fluorophenyl)cyclohexyl)but-3-enoic acid (37.3 mg, 0.142 mmol) in MeOH (10 mL) was added about 50 mg of 10% Pd/C (50% wet) and the solution was stirred under $H_2$ (50 psi) for 4 hrs. After removal of the catalyst by filtering thru Celite, the solvent was evaporated off to give 4-(1-(4-fluorophenyl)cyclohexyl)butanoic acid (30 mg, 0.113 mmol, 80% yield) as an oil. $^1$H NMR (400 MHz, CDCl$_3$) δ ppm 9.80 (1 H, br. s.), 7.42-7.49 (1 H, m), 7.21-7.27 (2 H, m), 6.98 (2 H, t, J=8.79 Hz), 2.11 (2 H, t, J=7.47 Hz), 1.97-2.07 (2 H, m), 1.17-1.61 (10 H, m).

Intermediate 7

4-(1-Phenylcyclohexyl)butanoic acid

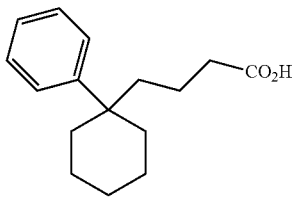
(Int. 7)

Int. 7A: 2-Allyl-2-phenylcyclohexanone

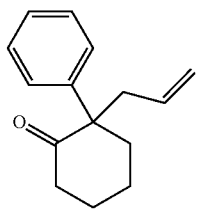
(Int. 7A)

To a solution of 2-phenylcyclohexanone (2 g, 11.48 mmol) in 50 ml of anhydrous DME in an ice bath was added 1M sodium bis(trimethylsilyl)amide (12.63 mL, 12.63 mmol) dropwise and the solution was stirred at the same temp for 20 minutes. In a separated flask allylpalladium chloride dimer (0.104 g, 0.287 mmol) was dissolved in 10 ml of anhydrous DME, and triphenylphosphine (0.151 g, 0.574 mmol) was added to the solution. It was stirred for 20 minutes at room temp and then allyl acetate (1.300 mL, 12.05 mmol) was added. This solution was added to the anion solution dropwise and the mixture was stirred at room temp for 2 hrs. The reaction was quenched with saturated NH$_4$Cl and extracted with hexane. The organic layer was washed with brine. The combine aqueous layers were back-extracted with hexane once and combined. Dried over Na$_2$SO$_4$ and evaporated to give an oily residue. It was purified by Combiflash (120 g silica gel) eluting with hexane followed by 1:9 EtOAc-hexane to give 2.24 g of 2-allyl-2-phenylcyclohexanone. $^1$H NMR (400 MHz, CDCl$_3$) δ ppm 7.35 (2 H, t, J=7.58 Hz), 7.21-7.27 (1 H, m), 7.12-7.18 (2 H, m), 5.35-5.52 (1 H, m), 4.82-4.97 (2 H, m), 2.61-2.72 (1 H, m), 2.39-2.55 (2 H, m), 2.24-2.38 (2 H, m), 1.89-1.99 (1 H, m, J=9.39, 6.15, 2.88, 2.88 Hz), 1.62-1.81 (4 H, m).

Int. 7B: (1-Allylcyclohexyl)benzene

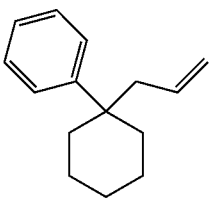
(Int. 7B)

To a solution of 2-allyl-2-phenylcyclohexanone (1.97 g, 9.19 mmol) in ethylene glycol (8 mL, 143 mmol) were added hydrazine (0.8 mL, 25 5 mmol) and potassium hydroxide (1.547 g, 27 6 mmol), and the mixture was stirred at 100° C. for 1 hr and refluxed in a 180° C. oil bath for 2.5 hrs. TLC showed that the hydrazone formation nearly complete. Then the excess hydrazine and water were distilled out in a 200° C. oil bath, and it was continued to heat at the same temperature for 4 hrs. After cooling to room temperature, the mixture was added to ether and washed with water and brine. The combined aqueous layers were back-extracted with ether (2×), combined, dried over Na$_2$SO$_4$, and evaporated to give an oily residue. It was purified by Combiflash (80 g silica gel) eluting with hexane followed by 5:95 EtOAc-hexane to give product (825 mg).

$^1$H NMR (400 MHz, CDCl$_3$) δ ppm 7.31 (4 H, d, J=4.39 Hz), 7.17 (1 H, dq, J=4.39, 4.25 Hz), 5.32-5.45 (1 H, m), 4.89 (1 H, s), 4.83-4.87 (1 H, m), 2.26 (2 H, d, J=7.47 Hz), 2.07 (2 H, dd, J=13.84, 6.59 Hz), 1.33-1.63 (8 H, m).

Int. 7C: 2-(1-Phenylcyclohexyl)acetaldehyde

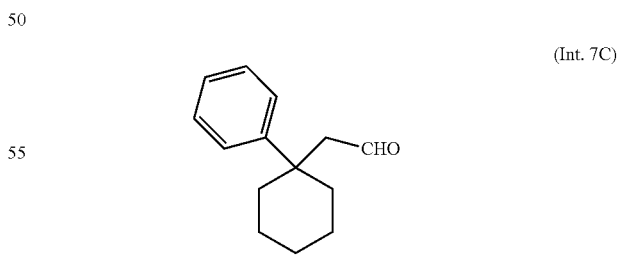
(Int. 7C)

To a solution of (1-allylcyclohexyl)benzene (210 mg, 1.048 mmol) in THF (5 mL) were added a solution of sodium periodate (538 mg, 2.52 mmol) in water (5.00 mL) and 0.105 ml of 2.5% OsO$_4$ in t-BuOH. The mixture was stirred at room temperature for 18 hrs. The mixture was extracted with EtOAc and washed with brine. The combined aqueous layers were back extracted with EtOAc and combined. The resulting material was dried over Na$_2$SO$_4$ and evaporated to give an oily residue. $^1$H NMR (400 MHz, CDCl$_3$) δ ppm 9.36 (2 H, t, J=3.08 Hz), 7.18-7.42 (5 H, m), 2.58 (2 H, d, J=3.30 Hz), 1.34-1.81 (10 H, m).

Int. 7D: (E)-Ethyl 4-(1-phenylcyclohexyl)but-2-enoate

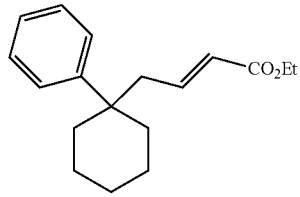

(Int. 7D)

To a solution of triethyl phosphonoacetate (0.601 mL, 3.00 mmol) in THF (10 mL) at 0° C. was added 1 M potassium tert-butoxide (3.00 mL, 3.00 mmol) in THF dropwise and the mixture was stirred for 30 mins at the same temperature. Then a solution of 2-(1-phenylcyclohexyl)acetaldehyde (405 mg, 2 0 mmol) in 4 ml of THF was added dropwise and the mixture was stirred for 0.5 hrs at 0° C. and for 1.5 hrs at room temperature. The mixture was added to EtOAc and washed with water (2×) and saturated NH$_4$Cl. The resulting material was dried over Na$_2$SO$_4$ and evaporated to give an oily residue. It was purified by Combiflash (80 g silica gel) eluting with 5:95 EtOAc-hexane to give (E)-ethyl 4-(1-phenylcyclohexyl)but-2-enoate (213.7 mg). $^1$H NMR (400 MHz, CDCl$_3$) δ ppm 7.27-7.37 (4 H, m), 7.15-7.23 (1 H, m), 6.60 (1 H, ddd, J=15.49, 7.91, 7.80 Hz), 5.66 (1 H, dt, J=15.60, 1.32 Hz), 4.12 (2 H, q, J=7.18 Hz), 2.39 (2 H, dd, J=7.80, 1.21 Hz), 2.11 (2 H, dd, J=13.07, 5.60 Hz), 1.33-1.66 (8 H, m), 1.24 (3 H, t, J=7.18 Hz).

Int. 7E: Ethyl-4-(1-phenylcyclohexyl)butanoate

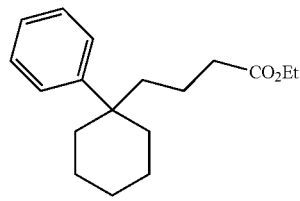

(Int. 7E)

To a solution of (E)-ethyl 4-(1-phenylcyclohexyl)but-2-enoate (140 mg, 0.514 mmol) in MeOH (15 mL) was added about 50 mg of 10% Pd/C and the mixture was stirred under H$_2$ (30 psi) for 1 hr. The catalyst was filtered off and the filtrate was evaporated to give ethyl 4-(1-phenylcyclohexyl)butanoate as an oil. $^1$H NMR (400 MHz, CDCl$_3$) δ ppm 7.31 (2 H, s), 7.30 (2 H, s), 7.13-7.20 (1 H, m), 4.06 (2 H, q, J=7.03 Hz), 2.04-2.13 (4 H, m), 1.33-1.63 (10 H, m), 1.24-1.32 (2 H, m), 1.20 (3 H, t, J=7.14 Hz).

Int. 7: 4-(1-Phenylcyclohexyl)butanoic acid

To a solution of ethyl 4-(1-phenylcyclohexyl)butanoate (0.211 g, 0.77 mmol) in MeOH (5 mL) was added 1M sodium hydroxide (1.155 mL, 1.155 mmol) and the mixture was stirred at room temperature for 5 hrs. Then an additional 0.39 ml of 1M NaOH was added and stirring was continued for 3 hrs. To the mixture was added 2 ml of 1N HCl and extracted with EtOAc (2×). The combined extracts were washed with brine, dried over Na$_2$SO$_4$ and evaporated to give an oily residue, which became white solid upon storing at room temperature.

Intermediate 8

4-(6-Phenyl-1,4-dioxaspiro[4.5]decan-6-yl)butanoic acid

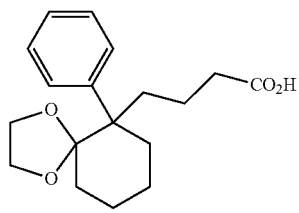

(Int. 8)

Int. 8A: 6-Allyl-6-phenyl-1,4-dioxaspiro[4.5]decane

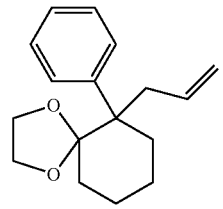

(Int. 8A)

A solution of 2-allyl-2-phenylcyclohexanone (370 mg, 1.727 mmol), ethylene glycol (0.481 mL, 8.63 mmol), and tosic acid (32.8 mg, 0.173 mmol) in benzene (10 mL) was refluxed under Dean-Stark trap for 1.5 hrs. Then an additional 0.3 ml of ethylene glycol and ~20 mg of tosic acid were added and the mixture was refluxed for an additional 15 hrs. After cooling, 2 ml of saturated NaHCO$_3$ was added and the product was extracted with EtOAc. The extract was washed with brine, and the combined aqueous layers were back-extracted with EtOAc once and combined. The extracts were dried over Na$_2$SO$_4$ and evaporated to give an oily residue. It was purified by Combiflash (40 g silica gel) eluting with 1:9 EtOAc-hexane to give 444.5 mg of ketal as an oil. $^1$H NMR (400 MHz, CDCl$_3$) δ ppm 7.56 (2 H, d, J=7.25 Hz), 7.24-7.31 (2 H, m), 7.15-7.21 (1 H, m), 5.22-5.35 (1 H, m), 4.99 (1 H, d, J=16.70 Hz), 4.86 (1 H, d, J=10.11 Hz), 3.77 (1 H, q, J=7.03 Hz), 3.67 (1 H, td, J=6.87, 4.94 Hz), 3.57 (1 H, td, J=6.76, 4.94 Hz), 2.85-3.04 (2 H, m), 2.67 (1 H, dd, J=14.39, 8.68 Hz), 2.26 (1 H, ddd, J=13.68, 8.84, 5.16 Hz), 1.50-1.92 (7 H, m).

Int. 8B: 2-(6-Phenyl-1,4-dioxaspiro[4.5]decan-6-yl)acetaldehyde

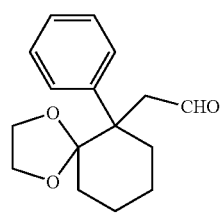

(Int. 8B)

To a solution of 6-allyl-6-phenyl-1,4-dioxaspiro[4.5]decane (444 mg, 1.719 mmol) in THF (5 mL) was added a solution of sodium periodate (441 mg, 2.062 mmol) in water (5.00 mL), and 0.175 ml of 2.5% OsO₄ in t-BuOH, and the mixture was stirred for 3 hrs. Next, the stirring was stopped and the mixture was added to EtOAc and washed with water, aq. Na₂S₂O₃, and brine. The resulting material was dried over Na₂SO₄ and evaporated to give an oily residue.

Int. 8C: (E)-Methyl 4-(6-phenyl-1,4-dioxaspiro[4.5]decan-6-yl)but-2-enoate

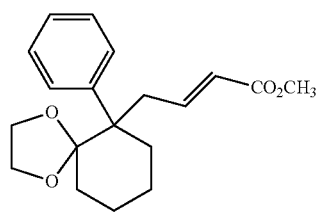

(Int. 8C)

A solution of 2-(6-phenyl-1,4-dioxaspiro[4.5]decan-6-yl) acetaldehyde (0.448 g, 1.72 mmol) and methyl (triphenylphosphoranylidene)-acetate (1.150 g, 3.44 mmol) in THF (7 mL) was refluxed for 18 hrs. After cooling, solvent was evaporated and the residue was purified by Combiflash (40 g silica gel) eluting with 1:9 EtOAc-hexane to give (E)-methyl 4-(6-phenyl-1,4-dioxaspiro[4.5]decan-6-yl)but-2-enoate as an oil (136 mg). LC/MS: m/e 317.20 (M+H)⁺.

Int. 8D: Methyl 4-(6-phenyl-1,4-dioxaspiro[4.5]decan-6-yl)butanoate

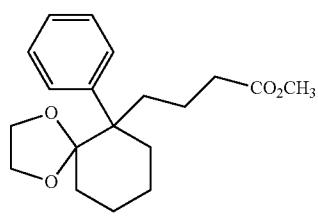

(Int. 8D)

To a solution of (E)-methyl 4-(6-phenyl-1,4-dioxaspiro[4.5]decan-6-yl)but-2-enoate (136 mg, 0.430 mmol) in MeOH (15 mL) was added about 50 mg of 10% Pd/C and the mixture was stirred under H₂ (25 psi) for 3.5 hrs. The mixture was filtered through Celite and evaporated to give an oily residue. LC/MS: m/e 319.10 (M+H)⁺.

Int. 8: 4-(6-Phenyl-1,4-dioxaspiro[4.5]decan-6-yl)butanoic acid

To a solution of methyl 4-(6-phenyl-1,4-dioxaspiro[4.5]decan-6-yl)butanoate (0.137 g, 0.43 mmol) in MeOH (3 mL) was added 1N sodium hydroxide (1.290 mL, 1.290 mmol), and the mixture was stirred at room temperature for 4 hrs. To the mixture was added 1.4 mL of 1N HCl and the product was extracted with EtOAc (2×). The combined extracts were washed with brine, dried over Na₂SO₄ and evaporated to give a solid residue (128 mg).

Intermediate 9

3-(4-(3-(Trifluoromethyl)phenyl)tetrahydro-2H-pyran-4-yl)propanoic acid

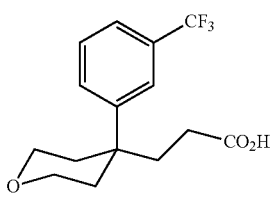

(Int. 9)

Int. 9A: 4-(3-(Trifluoromethyl)phenyl)tetrahydro-2H-pyran-4-carbonitrile (Int. 9A)

A solution of 2-(3-(trifluoromethyl)phenyl)acetonitrile (2 g, 10 8 mmol) in DMF (10 mL) was added dropwise to a suspension of sodium hydride (1.05 g, 26.3 mmol, 60% in oil dispersion) in DMF (10 mL) and cooled to 0° C. in an ice water bath. After addition, the mixture was warmed to room temperature and stirred for 30 min. The suspension was cooled to 0° C. and a solution of 1-chloro-2-(2-chloroethoxy)ethane (2 g, 13.98 mmol) in DMF (20 mL) was added dropwise over a period of 30 min. The dark suspension was warmed to room temperature and stirred for an additional 1.5 h. The mixture was quenched by addition of aq. 10% LiCl solution (50 mL) and diluted with EtOAc (100 mL). The organic extract was separated and the aqueous layer was extracted with EtOAc (30 mL, 2×). EtOAc extracts were combined, washed with 10% aq. LiCl solution (30 mL, 3×), and brine (25 mL, 2×), dried (MgSO₄), filtered, and concentrated to obtain a dark brown oil (HPLC and LC/MS). The crude oil was chromatographed on a silica gel column. Elution with 10% EtOAc in heptane, followed by 20% EtOAc in heptane afforded 4-(3-(trifluoromethyl)phenyl)tetrahydro-2H-pyran-4-carbonitrile as a light yellow solid (2.31 g, 84% yield). HPLC: $t_R$=2.75 min, YMC Combi S5 ODS 4.6×50 mm, 4 min gradient, Detection Wave length 220 nm, Starting solvent: 10% aq. MeOH-0.2% H₃PO₄; Final solvent: 90% aq. MeOH-0.2% H₃PO₄. LC/MS: m/e 256.06 (M+H)⁺, 229.02 (M+H-HCN)⁺.

Int. 9B: Ethyl 3-(4-(3-(trifluoromethyl)phenyl)tetrahydro-2H-pyran-4-yl)acrylate (Int. 9B)

A 1M solution of diisobutylaluminumhydride (18.34 mL, 18.34 mmol) in toluene was added dropwise to a solution of 4-(3-(trifluoromethyl)phenyl)tetrahydro-2H-pyran-4-carbonitrile (2.31 g, 9.17 mmol) in toluene (25 mL). The reaction mixture was stirred at room temperature for 4 h and diluted with EtOAc and 2 N aq. HCl solution. The organic layer was separated and the aqueous layer was extracted with EtOAc. The EtOAc extracts were combined, washed with 2N aq. HCl solution, brine, dried ($Na_2SO_4$), and evaporated under vacuum to yield 0.83 g of an orange oil which was chromatographed on silica gel (Teledyne-Isco RediSep 40 g column) Elution with 20% EtOAc in hexanes, followed by 30% EtOAc in hexanes afforded 4-(3-(trifluoromethyl)phenyl)-tetrahydro-2H-pyran-4-carbaldehyde (970 mg, 41% yield) as a yellow viscous oil. $^1$H NMR (400 MHz, $CDCl_3$): δ ppm 9.44 (s, 1H), 7.37-7.72 (m, 4H), 3.93 (ddd, 2 H), 3.60 (dt, 2H), 2.45 (d, 2H), 1.97-2.24 (m, 2H).

N,N-Diisopropylethylamine (2.95 mL, 16.9 mmol) and anhydrous lithium bromide (489 mg, 5.63 mmol) were added to a stirred solution of 4-(3-(trifluoromethyl)phenyl)-tetrahydro-2H-pyran-4-carbaldehyde (485 mg, 1.88 mmol) in THF (15 mL). After 20 min., triethyl phosphonoacetate (1.12 mL, 5.63 mmol) was added and the mixture was stirred at room temperature for 16 h. Additional N,N-diisopropylethylamine (980 μL, 5.64 mmol) was added and stirring was continued for additional 160 min. The reaction mixture was diluted with EtOAc and 1N aq. HCl solution. The organic layer was separated, washed with 1N aq. HCl solution, brine, dried ($Na_2SO_4$), filtered, and concentrated under vacuum to obtain a thin yellow oil which was chromatographed on silica gel (Teledyne-Isco RediSep 12 g column) Elution with 5%, 10%, and 20% EtOAc in hexanes afforded ethyl 34443-(trifluoromethyl)phenyl)tetrahydro-2H-pyran-4-yl)acrylate (569 mg, 92% yield) as a viscous yellow oil. $^1$H NMR (400 MHz, $CDCl_3$): δ ppm 7.38-7.68 (m, 4H), 6.98 (d, 1H), 5.71 (d, 1H), 4.19 (q, 2H), 3.76 (dd, 4H), 2.06-2.34 (m, 4H), 1.29 (t, 3H).

Int. 9: 3-(4-(3-(Trifluoromethyl)phenyl)tetrahydro-2H-pyran-4-yl)propanoic acid

A solution of ethyl 3-(4-(3-(trifluoromethyl)phenyl)tetrahydro-2H-pyran-4-yl)acrylate (101 mg, 308 μmol) and platinum(IV) oxide (10.3 mg, 46 μmol) in ethanol (2 mL) was hydrogenated at 1 atmosphere for 4.25 h. The catalyst was removed by filtration through a Whatman Autovial filter and the filtrate was concentrated under vacuum to afford ethyl 3-(4-(3-(trifluoromethyl)phenyl)tetrahydro-2H-pyran-4-yl) propanoate (99 mg, 97% yield) as a viscous colorless oil. 1H NMR (400 MHz, $CDCl_3$): δ ppm 7.34-7.60 (m, 4H), 4.02 (q, 2H), 3.81 (ddd, 2H), 3.43-3.63 (m, 2H), 2.07-2.23 (m, 2H), 1.97-2.04 (m, 2H), 1.84-1.96 (m, 4H), 1.19 (t, 3H).

A solution of ethyl 3-(4-(3-(trifluoromethyl)phenyl)tetrahydro-2H-pyran-4-yl) propanoate (99 mg, 302 μmol) in a 1:1 mixture of THF and MeOH (1.088 mL) was treated with a 2.78 M aq NaOH solution (544 μL, 1.512 mmol) and the mixture was stirred at room temperature for 80 min. The reaction mixture was concentrated and the residue was diluted with aq. 1N HCl solution (8 mL). After brief sonication (<1 min) a precipitation was observed. The precipitated solid was collected by filtration, washed several times with water, and dried under vacuum to obtain 3-(4-(3-(trifluoromethyl)phenyl)tetrahydro-2H-pyran-4-yl)propanoic acid (77 mg, 84% yield) as a white solid. $^1$H NMR (400 MHz, $CDCl_3$): δ ppm 7.38-7.62 (m, 4H), 3.81 (ddd, 2H), 3.54 (ddd, 2H), 2.08-2.29 (m, 2H, m), 1.93-2.04 (m, 4H, 1.84-1.93 (m, 2H).

Intermediate 10

3-(2-Phenyltetrahydro-2H-pyran-2-yl)propanoic acid

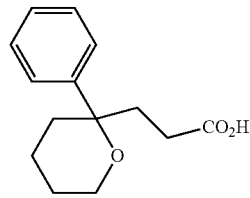

(Int. 10)

Int. 10A: 2-Phenyltetrahydro-2H-pyran-2-ol

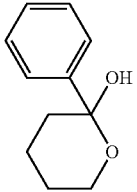

(Int. 10A)

To a solution of delta-valerolactone (1.854 mL, 19.98 mmol) in THF (20 mL) was added 1M phenylmagnesium bromide (19.98 mL, 19.98 mmol) dropwise at room temperature (exothermic), and the mixture was stirred at room temperature for 5 hrs. Then the reaction was quenched with saturated $NH_4Cl$ and extracted with EtOAc. The extract was washed with brine, and the combined aqueous layers were back extracted with EtOAc once and combined. The extracts were dried over $Na_2SO_4$ and evaporated to give an oily residue. It was purified by Combiflash (120 g silica gel) eluting with 4:6 followed by 1:1 EtOAc-hexane to give 1.97 g of 2-phenyltetrahydro-2H-pyran-2-ol as oil.

$^1$H NMR (400 MHz, $CDCl_3$) δ ppm 7.92-8.00 (1 H, m), 7.17-7.60 (5 H, m), 3.67 (1 H, t, J=6.15 Hz), 3.03 (1 H, t, J=7.14 Hz), 2.25-2.37 (1 H, m), 1.75-1.92 (2 H, m), 1.54-1.71 (2 H, m), 1.30-1.43 (1 H, m).

Int. 10B: 2-Allyl-2-phenyltetrahydro-2H-pyran

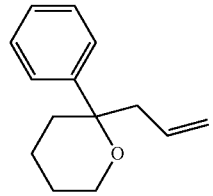

(Int. 10B)

To a solution of 2-phenyltetrahydro-2H-pyran-2-ol (1.066 g, 5.98 mmol) and allyltrimethylsilane (1.901 mL, 11.96 mmol) in $CH_2Cl_2$ (25 mL) at 0° C. was added $BF_3.OEt_2$ (0.758 mL, 5.98 mmol) dropwise, and the mixture was stirred at the same temperature for 1 hr. Then the reaction was quenched with saturated $NaHCO_3$ and the product was extracted with EtOAc. The extract was washed with brine, and the combined aqueous layers were back extracted with EtOAc once and combined. The extracts were dried over Na₂SO₄ and evaporated to give an oily residue. It was purified by Combiflash (80 g silica gel) eluting with 1:9 followed by 4:6 EtOAc-hexane to give 2-allyl-2-phenyltetrahydro-2H-pyran as oil (0.954 g). $^1$H NMR (400 MHz, CDCl₃) δ ppm 7.10-7.45 (5 H, m), 5.47-5.65 (1 H, m, J=17.19, 10.11, 7.33, 7.33 Hz), 4.84-5.00 (2 H, m), 3.64-3.78 (1 H, m), 3.41-3.57 (1 H, m), 2.35-2.48 (1 H, m), 2.20-2.35 (1 H, m), 1.55-1.81 (4 H, m), 1.35-1.54 (2 H, m).

Int. 10C: 3-(2-Phenyltetrahydro-2H-pyran-2-yl)propan-1-ol

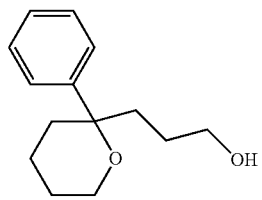

(Int. 10C)

To a solution of 2-allyl-2-phenyltetrahydro-2H-pyran (700 mg, 3.46 mmol) in THF (7 mL) at 0° C. was added 1M borane tetrahydrofuran complex (1.730 mL, 1.730 mmol) dropwise, and the mixture was stirred overnight at room temperature. After cooling to 0° C., water (0.07 ml) was added to destroy the excess borane. After stirring for 10 mins, 3M NaOH (0.42 mL, 1.260 mmol) was added and stirred for 10 mins. Then 30% H₂O₂ (0.42 mL, 4.11 mmol) was added and the cooling bath was removed. It was refluxed for 1.5 hrs and cooled to room temperature. It was extracted with EtOAc (2×), and the combined extracts were washed with brine, dried over Na₂SO₄ and evaporated to give 3-(2-phenyltetrahydro-2H-pyran-2-yl)propan-1-ol as oil. $^1$H NMR (400 MHz, CDCl₃) δ ppm 7.11-7.44 (5 H, m), 3.66-3.81 (2 H, m), 3.48-3.59 (2 H, m), 2.22-2.37 (2 H, m), 1.35-1.89 (8 H, m).

Int. 10: 3-(2-Phenyltetrahydro-2H-pyran-2-yl)propanoic acid

To a solution of 3-(2-phenyltetrahydro-2H-pyran-2-yl)propan-1-ol (640 mg, 2.91 mmol) in acetone (10 mL) at 0° C. was added 4.15 mL of 0.7 M Jones reagent, and the mixture was stirred for 30 mins at 0° C. and for 1 hr at room temperature. It was added to CH₂Cl₂ and washed with water twice. The extract was dried over Na₂SO₄ and evaporated to give an oily residue. The residue was purified by Combiflash (40 g silica gel) eluting with 4:6 EtOAc-hexane to 3-(2-phenyltetrahydro-2H-pyran-2-yl)propanoic acid (346 mg). LC/MS: m/e 235.21 (M+H)⁺.

Intermediate 11

2-(2-Phenyltetrahydro-2H-pyran-2-yl)acetic acid

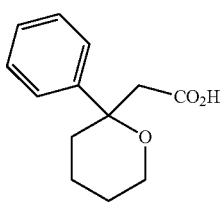

(Int. 11)

Int. 11A: 2-(2-Phenyltetrahydro-2H-pyran-2-yl)acetaldehyde

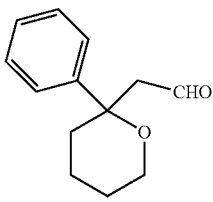

(Int. 11A)

To a solution of 2-allyl-2-phenyltetrahydro-2H-pyran (370 mg, 1.829 mmol, Int. 10B) in THF (2.5 mL) was added a solution of N-methylmorpholine-N-oxide (321 mg, 2.74 mmol) in water (2.5 mL), and then 0.37 mL of 2.5% OsO₄ in water was also added. The mixture was stirred at room temperature for 1 day. The reaction was quenched with aq Na₂S₂O₃ and the product was extracted with EtOAc. The extract was washed with brine, and the combined aqueous layers were back extracted with EtOAc once and combined. The extracts were dried over Na₂SO₄ and evaporated to give an oily residue. The residue was dissolved in MeOH (5 mL). A solution of sodium periodate (469 mg, 2.195 mmol) in water (5 mL) was added dropwise at 0° C. As soon as the addition started, white precipitate formed. The mixture was stirred for 30 mins at the same temperature and poured into EtOAc. The extract was washed with brine, and the combined aqueous layers were back extracted with EtOAc and combined. The extracts were dried over Na₂SO₄ and evaporated to give an oily residue. The residue was purified by Combiflash (40 g silica gel) eluting with 1:9 EtOAc-hexane to give 2-(2-phenyltetrahydro-2H-pyran-2-yl)acetaldehyde as an oil (239 mg). $^1$H NMR (400 MHz, CDCl₃) δ ppm 9.64-9.68 (1 H, m), 7.36-7.46 (4 H, m), 7.25-7.31 (1 H, m), 3.74-3.81 (1 H, m), 3.55-3.64 (1 H, m), 2.58-2.75 (2 H, m), 2.29-2.39 (1 H, m), 1.80-1.92 (1 H, m), 1.59-1.75 (2 H, m), 1.40-1.58 (2 H, m).

Int. 11: 2-(2-Phenyltetrahydro-2H-pyran-2-yl)acetic acid

To a solution of 2-(2-phenyltetrahydro-2H-pyran-2-yl)acetaldehyde (100 mg, 0.490 mmol) and sulfamic acid (57.0 mg, 0.587 mmol) in THF (1.5 mL) was added a solution of sodium chlorite (53.1 mg, 0.587 mmol) in water (1.5 mL) dropwise, and the mixture was stirred at room temperature for 3 hrs. Then the product was extracted with EtOAc (3×) and the combined extracts were washed with brine, dried over Na₂SO₄, and evaporated to give 2-(2-phenyltetrahydro-2H-pyran-2-yl)acetic acid as oil. LC/MS: m/e 221.14 (M+H)⁺.

Intermediate 12

2-((1-(4-Fluorophenyl)cyclohexyl)methoxy)acetic acid

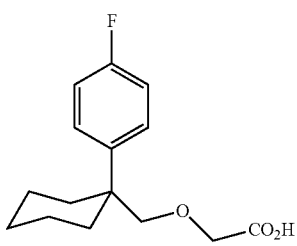

(Int. 12)

A solution of (1-(4-fluorophenyl)cyclohexyl)methanol (108 mg, 521 μmol) in toluene was cooled to 0° C. and treated with a 50% aq. NaOH solution (500 μL) followed by tetrabutylammonium hydrogen sulfate (44 mg, 130 μmol). The mixture was stirred at 0° C. for 30 min and tert-butyl bromoacetate (152 mg, 781 μmol) was added. The ice bath was removed, and stirring was continued at room temperature for 2 h. The reaction mixture was diluted with EtOAc and water. The organic layer was separated, washed with water, brine, dried (Na₂SO₄), and concentrated. The crude oil was chromatographed on silica gel (Teledyne-Isco RediSep 12 g silica gel column) and eluted with hexanes, followed by 1% and 3% EtOAc in hexanes to obtain tert-butyl 2-((1-(4-fluorophenyl)cyclohexyl)methoxy)acetate (100 mg, 60% yield) as a colorless viscous oil. ¹H NMR (400 MHz, CDCl₃): δ ppm 7.28-7.46 (m, 2H), 6.92-7.09 (m, 2H), 3.78 (s, 2H), 3.39 (s, 2H), 2.09 (d, 2H), 1.67-1.86 (m, 2H), 1.47-1.59 (m, 4H), 1.44 (s, 9H), 1.31-1.38 (m, 2H).

A solution of tert-butyl 2-((1-(4-fluorophenyl)cyclohexyl)methoxy)acetate (100 mg, 310 μmol) in trifluoroacetic acid (1 mL) was stirred at room temperature for 85 min. TFA was removed under reduced pressure, followed by co-evaporation with ether to obtain the crude 2-((1-(4-fluorophenyl)cyclohexyl)methoxy)acetic acid (79 mg, 96% yield) as a white solid. ¹H NMR (400 MHz, CDCl₃): δ ppm 7.30-7.43 (m, 2H), 6.93-7.17 (m, 2H), 3.91 (s, 2H), 3.46 (s, 2H), 2.13 (d, 2H), 1.60-1.76 (m, 2H), 1.55 (dd, 3H), 1.26-1.44 (m, 3H).

Intermediate 13

2-((1-(4-Chlorophenyl)cyclobutyl)methoxy)acetic acid

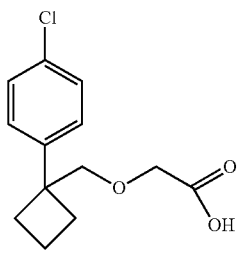

(Int. 13)

A solution of (1-(4-chlorophenyl)cyclobutyl)methanol (1.5 g, 7.63 mmol) in toluene (21 mL) was cooled to 0° C. and treated with a 33% aq. NaOH solution (7.43 mL) followed by tetrabutylammonium hydrogen sulfate (647 mg, 1.91 mmol). The mixture was stirred at 0° C. for 10 min and tert-butyl bromoacetate (1.11 mL, 7.63 mmol) was added. The ice bath was removed, and stirring was continued at room temperature for 50 min. Additional tert-butyl bromoacetate (1.11 mL, 7.63 mmol) was added and the mixture was stirred at room temperature for 16 h. Additional tert-butyl bromoacetate (1.11 mL, 7.63 mmol) was added and the mixture was stirred at room temperature for additional 24 h. The reaction mixture was diluted with EtOAc and water. The organic layer was separated, washed with water, brine, dried (Na₂SO₄), and concentrated. The crude oil was chromatographed on silica gel (Teledyne-Isco RediSep 80 g silica gel column) and eluted with hexanes, followed by 1% and 2% EtOAc in hexanes to obtain tert-butyl 2-((1-(4-chlorophenyl)cyclobutyl)methoxy) acetate (1.77 g, 75% yield) as a white solid. 1H NMR (400 MHz, CDCl₃): δ ppm 7.25-7.28 (2 H, m), 7.06-7.19 (2 H, m), 3.85 (2 H, s), 3.64 (2 H, s), 2.22-2.49 (4 H, m), 1.98-2.18 (1 H, m), 1.73-1.93 (1 H, m), 1.45 (9 H, s).

A solution of tert-butyl 2-((1-(4-fluorophenyl)cyclohexyl)methoxy)acetate (1.77 g, 5.69 mmol) in trifluoroacetic acid (40 mL) was stirred at room temperature for 37 min. TFA was removed under reduced pressure, followed by co-evaporation with ether to obtain the crude 2-((1-2-((1-(4-chlorophenyl)cyclobutyl)methoxy)acetic acid (1.36 g, 94% yield) as a white solid. ¹H NMR (400 MHz, CDCl₃): δ ppm 7.27-7.33 (2 H, m), 6.97-7.19 (2 H, m), 3.99 (2 H, s), 3.71 (2 H, s), 2.21-2.45 (4 H, m), 1.99-2.20 (1 H, m), 1.78-1.98 (1 H, m).

Example 1

3-(5-(2-(1-(3,5-Difluorophenyl)cyclohexyl)ethyl)-1,2,4-oxadiazol-3-yl)-6-methyl-2(1H)-pyridinone

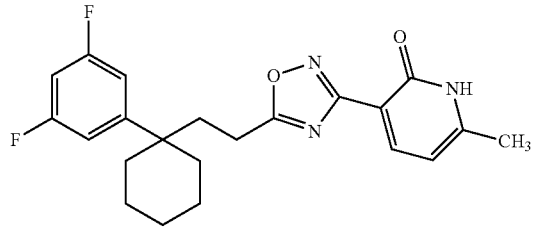

(1)

To a solution of 3-(1-(3,5-difluorophenyl)cyclohexyl)propanoic acid (20 mg, 0.075 mmol) and (Z)—N'-hydroxy-6-methyl-2-oxo-1,2-dihydropyridine-3-carboximidamide (12.46 mg, 0.075 mmol) in acetonitrile (1 mL) was added N,N'-diisopropylcarbodiimide (0.013 mL, 0.082 mmol), and the mixture was stirred for 2.5 hrs at room temp. TBAF (0.112 mL, 0.112 mmol) was added and the mixture was stirred at room temperature. The oxadiazole formation was very slow. After 1 day of stirring, an additional 0.112 mL of 1M TBAF was added and the mixture was stirred for 5 more days. The mixture was diluted with EtOAc and washed with water and brine. The organic extract was dried over Na₂SO₄ and evaporated to give an oily residue which was purified by Combiflash (12 g silica gel). Elution with 7:93 MeOH—CH₂Cl₂ afforded a white solid which was repurified by prep HPLC to give pure 3-(5-(2-(1-(3,5-difluorophenyl)cyclohexyl)ethyl)-1,2,4-oxadiazol-3-yl)-6-methylpyridin-2(1H)-one (8.0 mg, 26.7% yield) as a white solid. HPLC: t$_R$=3.95 min, Waters Sunfire C18 4.6×50 mm, 4 min gradient, Detection Wave length 220 nm, Starting solvent: 10% aq. MeOH-0.1% TFA; Final solvent: 90% aq. MeOH-0.1% TFA. LC/MS: m/e 400.12 (M+H)⁺. ¹H NMR (400 MHz, CDCl₃): δ ppm 8.19 (1 H, d), 6.84-6.86 (2 H, m), 6.65 (1H, m), 6.21 (1H, d), 2.44-2.54 (5 H, m), 2.04-2.06 (4 H, m), 1.39-1.61 (8 H, m).

Example 2

4-(5-(2-(1-(3,5-Difluorophenyl)cyclohexyl)ethyl)-1,2,4-oxadiazol-3-yl)-2(1H)-pyridinone

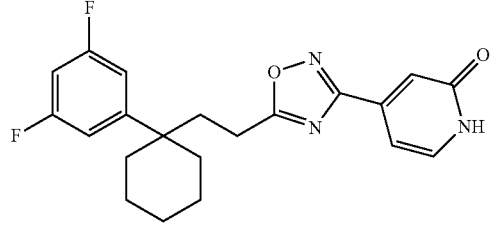

(2)

To a solution of 3-(1-(3,5-difluorophenyl)cyclohexyl)propanoic acid (20 mg, 0.075 mmol) and (Z)—N'-hydroxy-2-oxo-1,2-dihydropyridine-4-carboximidamide (11.42 mg, 0.075 mmol) in acetonitrile (1 mL) was added N,N'-diisopropylcarbodiimide (0.013 mL, 0.082 mmol), and the mixture was stirred for 2.5 hrs at room temp. TBAF (0.112 mL, 0.112 mmol) was added and the mixture was stirred for 40 hrs at room temp. After addition of EtOAc the mixture was washed with water and brine, dried over $Na_2SO_4$ and evaporated to give an oily residue which was purified by Combiflash (12 g silica gel). Elution with 7:93 MeOH—$CH_2Cl_2$ gave a white solid residue which was repurified by prep HPLC to give 4-(5-(2-(1-(3,5-difluorophenyl)cyclohexyl)ethyl)-1,2,4-oxadiazol-3-yl)pyridin-2(1H)-one (4.8 mg, 16.64% yield) as a white solid. HPLC: $t_R$=3.95 min, Waters Sunfire C18 4.6×50 mm, 4 min gradient, Detection Wave length 220 nm, Starting solvent: 10% aq. MeOH-0.1% TFA; Final solvent: 90% aq. MeOH-0.1% TFA. LC/MS: m/e 386.13 $(M+H)^+$. $^1$H NMR (400 MHz, $CDCl_3$): δ ppm 7.45 (1 H, d), 7.24 (1H, s), 6.84-6.88 (3 H, m), 6.65 (1H, m), 2.56-2.6 (2 H, m), 2.05-2.07 (4 H, m), 1.23-1.63 (8 H, m).

Examples 3 to 42

Examples 3 to 42 were synthesized according to the following general protocol: The appropriate amidoxime (90 mmol) was added to a solution of 3-(1-phenylcyclohexyl)propanoic acid (17.42 mg, 80 mmol), EDAC (15.82 mg, 83 mmol), HOBT (11.15 mg, 83 mmol), and N,N-diisopropylethylamine (14.4 μL, 83 mmol) in DMF (750 μL). The solution was agitated at room temperature for 30 min. The reaction mixture was diluted with DMF (250 μL) and then heated to 125° C. overnight. The reaction mixture was then purified by automated preparative HPLC (Waters XBridge 19×100 mm 5 μm C18, Flow rate 20 mL/min, Gradient time 15 min, Mobile Phase: solvent A: 5% aq. MeOH, 0.05% TFA; solvent B: 95% aq. MeOH, 0.05% TFA).

| Ex. | R | Name | HPLC retention time (min) | Observed Mass $(M + H)^+$ |
|---|---|---|---|---|
| 3 | 3-fluoro-4-methylphenyl | 3-(3-fluoro-4-methylphenyl)-5-(2-(1-phenylcyclohexyl)ethyl)-1,2,4-oxadiazole | 4.12[a] | 364.96 |
| 4 | 3,5-bis(trifluoromethyl)phenyl | 3-(3,5-bis(trifluoromethyl)phenyl)-5-(2-(1-phenylcyclohexyl)ethyl)-1,2,4-oxadiazole | 4.31[a] | 468.87 |
| 5 | 4-fluorophenyl | 3-(4-fluorophenyl)-5-(2-(1-phenylcyclohexyl)ethyl)-1,2,4-oxadiazole | 3.92[a] | 350.97 |
| 6 | 4-methylphenyl | 3-(4-methylphenyl)-5-(2-(1-phenylcyclohexyl)ethyl)-1,2,4-oxadiazole | 4.03[a] | 347.00 |
| 7 | phenyl | 3-phenyl-5-(2-(1-phenylcyclohexyl)ethyl)-1,2,4-oxadiazole | 3.89[a] | 332.99 |
| 8 | 3-(trifluoromethyl)phenyl | 5-(2-(1-phenylcyclohexyl)ethyl)-3-(3-(trifluoromethyl)phenyl)-1,2,4-oxadiazole | 4.13[a] | 400.95 |

-continued

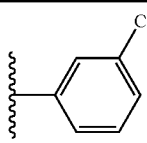

| Ex. | R | Name | HPLC retention time (min) | Observed Mass (M + H)+ |
|---|---|---|---|---|
| 9 | 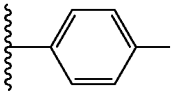 | 3-(3-methylphenyl)-5-(2-(1-phenylcyclohexyl)ethyl)-1,2,4-oxadiazole | 4.05$^a$ | 347.01 |
| 10 | 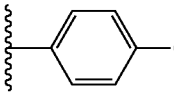 | 3-(4-chlorophenyl)-5-(2-(1-phenylcyclohexyl)ethyl)-1,2,4-oxadiazol | 4.13$^a$ | 366.94 |
| 11 | 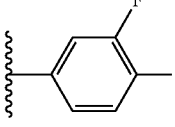 | 5-(2-(1-phenylcyclohexyl)ethyl)-3-(4-(trifluoromethyl)phenyl)-1,2,4-oxadiazole | 4.12$^a$ | 400.93 |
| 12 | 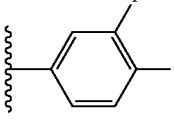 | 3-(3,4-difluorophenyl)-5-(2-(1-phenylcyclohexyl)ethyl)-1,2,4-oxadiazole | 3.83$^a$ | 368.97 |
| 13 | 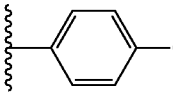 | 3-(3-fluoro-4-(trifluoromethyl)phenyl)-5-(2-(1-phenylcyclohexyl)ethyl)-1,2,4-oxadiazole | 4.03$^a$ | 418.94 |
| 14 | 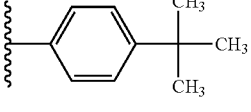 | 3-(4-methoxyphenyl)-5-(2-(1-phenylcyclohexyl)ethyl)-1,2,4-oxadiazole | 3.83$^a$ | 362.99 |
| 15 | 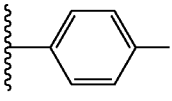 | 3-(4-tert-butylphenyl)-5-(2-(1-phenylcyclohexyl)ethyl)-1,2,4-oxadiazole | 4.14$^a$ | 416.94 |
| 16 | 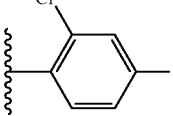 | 5-(2-(1-phenylcyclohexyl)ethyl)-3-(4-(trifluoromethoxy)phenyl)-1,2,4-oxadiazole | 4.12$^a$ | 493.90 |
| 17 | 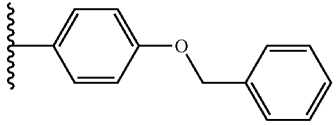 | 3-(2,4-dichlorophenyl)-5-(2-(1-phenylcyclohexyl)ethyl)-1,2,4-oxadiazole | 4.17$^a$ | 400.87 |
| 18 |  | 3-(4-(benzyloxy)phenyl)-5-(2-(1-phenylcyclohexyl)ethyl)-1,2,4-oxadiazole | 4.15$^a$ | 438.98 |

-continued

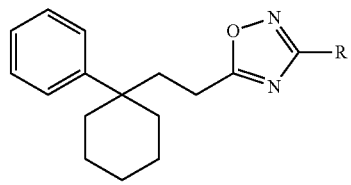

| Ex. | R | Name | HPLC retention time (min) | Observed Mass (M + H)+ |
|---|---|---|---|---|
| 19 | 3,5-dimethoxyphenyl (OCH3 at 3,5) | 3-(3,5-dimethoxyphenyl)-5-(2-(1-phenylcyclohexyl)ethyl)-1,2,4-oxadiazole | 3.88ª | 392.97 |
| 20 | 4-((2-fluorobenzyl)oxy)phenyl | 3-(4-((2-fluorobenzyl)oxy)phenyl)-5-(1-phenylcyclohexyl)ethyl)-1,2,4-oxadiazole | 4.15ª | 456.96 |
| 21 | 3-(((4-chlorophenyl)sulfonyl)methyl)phenyl | 3-(3-(((4-chlorophenyl)sulfonyl)methyl)phenyl)-5-(2-(1-phenylcyclohexyl)ethyl)-1,2,4-oxadiazole | 3.85ª | 520.85 |
| 22 | 4-((2-methyl-1,3-thiazol-4-yl)methoxy)phenyl | 3-(4-((2-methyl-1,3-thiazol-4-yl)methoxy)phenyl)-5-(2-(1-phenylcyclohexyl)ethyl)-1,2,4-oxadiazole | 3.75ª | 459.93 |
| 23 | 4-((2-chloro-1,3-thiazol-5-yl)methoxy)phenyl | 3-(4-((2-chloro-1,3-thiazol-5-yl)methoxy)phenyl)-5-(2-(1-phenylcyclohexyl)ethyl)-1,2,4-oxadiazole | 4.06ª | 479.87 |
| 24 | 3-((4,5-dichloro-1H-imidazol-1-yl)methyl)phenyl | 3-(3-((4,5-dichloro-1H-imidazol-1-yl)methyl)phenyl)-5-(2-(1-phenylcyclohexyl)ethyl)-1,2,4-oxadiazole | 3.82ª | 480.88 |
| 25 | 4-((2,4-dichlorobenzyl)oxy)phenyl | 3-(4-((2,4-dichlorobenzyl)oxy)phenyl)-5-(2-(1-phenylcyclohexyl)ethyl)-1,2,4-oxadiazole | 4.51ª | 506.84 |

-continued

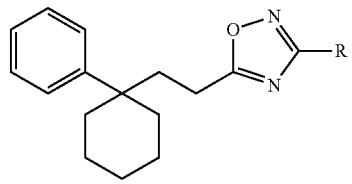

| Ex. | R | Name | HPLC retention time (min) | Observed Mass (M + H)+ |
|---|---|---|---|---|
| 26 | 2,5-dimethoxyphenyl (H3CO, OCH3) | 3-(2,5-dimethoxyphenyl)-5-(2-(1-phenylcyclohexyl)ethyl)-1,2,4-oxadiazole | 3.58[a] | 392.98 |
| 27 | 4-((4-chlorobenzyl)oxy)phenyl | 3-(4-((4-chlorobenzyl)oxy)phenyl)-5-(2-(1-phenylcyclohexyl)ethyl)-1,2,4-oxadiazole | 4.27[a] | 472.92 |
| 28 | 2,4-difluorophenyl | 3-(2,4-difluorophenyl)-5-(2-(1-phenylcyclohexyl)ethyl)-1,2,4-oxadiazole | 3.84[a] | 368.95 |
| 29 | 2-amino-4-pyridinyl | 4-(5-(2-(1-phenylcyclohexyl)ethyl)-1,2,4-oxadiazol-3-yl)-2-pyridinamine | 0.92[b] | 349.2 |
| 30 | 2-pyridinyl | 2-(5-(2-(1-phenylcyclohexyl)ethyl)-1,2,4-oxadiazol-3-yl)pyridine | 4.09[c] | 334.10 |
| 31 | 5-chloro-2-methylphenyl | 3-(5-chloro-2-methylphenyl)-5-(2-(1-phenylcyclohexyl)ethyl)-1,2,4-oxadiazole | 1.42[b] | 381.2 |
| 32 | 2-chloro-4-pyridinyl | 2-chloro-4-(5-(2-(1-phenylcyclohexyl)ethyl)-1,2,4-oxadiazol-3-yl)pyridine | 1.3[b] | 368.2 |
| 33 | 2-amino-3-pyridinyl | 3-(5-(2-(1-phenylcyclohexyl)ethyl)-1,2,4-oxadiazol-3-yl)-2-pyridinamine | 0.94[b] | 349.2 |
| 34 | 4-pyridinyl N-oxide | 4-(5-(2-(1-phenylcyclohexyl)ethyl)-1,2,4-oxadiazol-3-yl)pyridine 1-oxide | 1.04[b] | 350.1 |

-continued

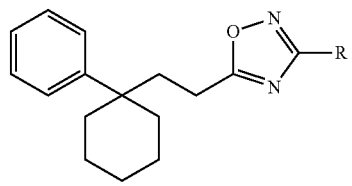

| Ex. | R | Name | HPLC retention time (min) | Observed Mass (M + H)+ |
|---|---|---|---|---|
| 35 | 2-methyl-1,3-thiazol-4-yl (CH₃) | 3-(2-methyl-1,3-thiazol-4-yl)-5-(2-(1-phenylcyclohexyl)ethyl)-1,2,4-oxadiazole | 1.19[b] | 354.1 |
| 36 | 4-((5-(trifluoromethyl)pyridin-2-yl)oxy)phenyl | 2-(4-(5-(2-(1-phenylcyclohexyl)ethyl)-1,2,4-oxadiazol-3-yl)phenoxy)-5-(trifluoromethyl)pyridine | 4.12[a] | 493.9 |
| 37 | pyridin-4-yl | 4-(5-(2-(1-phenylcyclohexyl)ethyl)-1,2,4-oxadiazol-3-yl)pyridine | 3.36[a] | 334.00 |
| 38 | pyridin-3-yl | 3-(5-(2-(1-phenylcyclohexyl)ethyl)-1,2,4-oxadiazol-3-yl)pyridine | 3.32[a] | 333.94 |
| 39 | 3-methylpyridin-2-yl | 3-methyl-2-(5-(2-(1-phenylcyclohexyl)ethyl)-1,2,4-oxadiazol-3-yl)pyridine | 3.35[a] | 347.82 |
| 40 | 3-methylthien-2-yl | 3-(3-methyl-2-thienyl)-5-(2-(1-phenylcyclohexyl)ethyl)-1,2,4-oxadiazole | 3.94[a] | 352.95 |

-continued

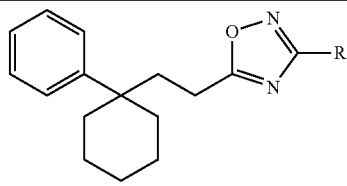

| Ex. | R | Name | HPLC retention time (min) | Observed Mass (M + H)+ |
|---|---|---|---|---|
| 41 | ![Cl, CH3 substituted phenyl] | 3-(2-chloro-4-methylphenyl)-5-(((1-(4-chlorophenyl)cyclobutyl)methoxy)methyl)-1,2,4-oxadiazole | 4.1[d] | 403.08 |

[a] Waters XBridge 4.6 × 50 mm 5 μm C18, Mobile Phase: solvent A: 5% aq. AcCN with 10 mM NH₄OAc; solvent B: 95% aq. AcCN with 10 mM NH₄OAc.
[b] BEH C18 42.1 × 50 mm 1.7 μ, Mobile Phase: solvent A: 100% H₂O, 0.05 % TFA; solvent B: 100% AcCN, 0.05% TFA.
[c] Chromolith SpeedROD 4.6 × 50 mm, Mobile Phase: solvent A: 10% aq. MeOH, 0.2% H₃PO₄; solvent B: 90% aq. MeOH, 0.2% H₃PO₄.
[d] YMC Combiscreen ODS-A 4.6 × 50 mm, Mobile Phase: solvent A: 10% aq. MeOH, 0.1% TFA; solvent B: 90% aq. MeOH, 0.1% TFA.

Comparative Example 42

3-Phenyl-5-(1-phenylcyclohexyl)-1,2,4-oxadiazole

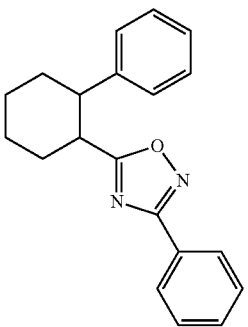

(42)

A solution of 1-phenylcyclohexanecarboxylic acid (1 g, 4.9 mmol), EDAC (1.032 g, 5.39 mmol), HOBT (825 mg, 5.39 mmol), and N,N-diisopropylethylamine (2.57 mL, 14.69 mmol) in DMF (5 mL) was stirred at room temperature for 30 min under an argon atmosphere. (E)-N'-hydroxybenzimidamide (733 mg, 5.39 mmol) was added and the reaction mixture was heated to 95° C. for 8 h. The reaction mixture was cooled to room temperature and a portion (~10%) was purified by automated preparative HPLC (PHENOMENEX® Luna Axia 21.2×100 mm 5 μm, Flow rate 20 mL/min, Gradient time 15 min, Mobile Phase: solvent A: 5% aq. MeOH, 0.05% TFA; solvent B: 95% aq. MeOH, 0.05% TFA). HPLC: $t_R$=3.95 min, Waters Sunfire C18 4.6×50 mm, 4 min gradient, Detection Wave length 220 nm, Starting solvent: 10% aq. MeOH-0.1% TFA; Final solvent: 90% aq. MeOH-0.1% TFA to obtain 3-phenyl-5-(1-phenylcyclohexyl)-1,2,4-oxadiazole (60 mg). LC/MS: m/e 305.2 (M+H)+. ¹H NMR (400 MHz, DMSO-$d_6$): δ ppm 7.95-8.14 (2 H, m), 7.47-7.66 (3H, m), 7.31-7.44 (4 H, m), 7.17-7.31 (1H, m), 2.57-2.75 (2 H, m), 2.01-2.18 (2 H, m), 1.71 (2H, bs), 1.51-1.65 (1H, m), 1.27-1.51 (3 H, m).

Biological Assays

S1P₁ Binding Assay

Membranes were prepared from CHO cells expressing human S1P1. Cells pellets (1×108 cells/pellet) were suspended in buffer containing 20 mM HEPES, pH 7.5, 50 mM NaCl, 2 mM EDTA and Protease Inhibitor cocktail (Roche), and disrupted on ice using the Polytron homogenizer. The homogenate was centrifuged at 20,000 rpm (48,000 g) and the supernatant was discarded. The membrane pellets were resuspended in buffer containing 50 mM HEPES, pH 7.5, 100 mM NaCl, 1 mM MgCl₂, 2 mM EDTA and stored in aliquots at −80° C. after protein concentration determination.

Membranes (2 μg/well) and 0.03 nM final concentration of 33P-S1P ligand (1 mCi/ml, American Radiolabeled Chemicals) diluted in assay buffer (50 mM HEPES, pH7.4, 5 mM MgCl₂, 1 mM CaCl₂, 0.5% fatty acid free BSA, 1 mM NaF) were added to the compound plates (384 Falcon v-bottom plate (0.5 Owen in a 11 point, 3-fold dilution). Binding was performed for 45 minutes at room temperature, terminated by collecting the membranes onto 384-well Millipore FB filter plates, and radioactivity was measured by TOPCOUNT®. The competition data of the test compounds over a range of concentrations was plotted as percentage inhibition of radioligand specific binding. The IC₅₀ is defined as the concentration of competing ligand needed to reduce specific binding by 50%.

Table A below lists S1P₁ Binding IC₅₀ values from the following examples of this invention measured in the S1P₁ binding assay described hereinabove. The results in Table A were rounded to two significant digits.

TABLE A

| Example No. | S1P1 Binding IC₅₀ (nM) |
|---|---|
| 1 | 1300 |
| 2 | 13 |
| 5 | 12 |
| 7 | 3.3 |
| 8 | 33 |
| 13 | 210 |

TABLE A-continued

| Example No. | S1P1 Binding IC$_{50}$ (nM) |
|---|---|
| 20 | 410 |
| 26 | 8.1 |
| 27 | 610 |
| 28 | 25 |
| 30 | 97 |
| 32 | 0.54 |
| 33 | 1.9 |
| 34 | 67 |
| 40 | 1.2 |

Receptor [35S] GTPγS Binding Assays

Compounds were loaded in a 384 Falcon v-bottom plate (0.5 μl/well in a 11 point, 3-fold dilution). Membranes prepared from S1P$_1$/CHO cells or EDG3-Ga15-bla HEK293T cells were added to the compound plate (40 μl/well, final protein 3 μg/well) with MULTIDROP®. [$^{35}$S]GTP (1250 Ci/mmol, Perkin Elmer) was diluted in assay buffer: 20 mM HEPES, pH7.5, 10 mM MgCl$_2$, 150 mM NaCl, 1 mM EGTA, 1 mM DTT, 10 μM GDP, 0.1% fatty acid free BSA, and 10 μg/ml Saponin to 0.4 nM. 40 μl of the [$^{35}$S] GTP solution was added to the compound plate with a final concentration of 0.2 nM. The reaction was kept at room temperature for 45 min. At the end of incubation, all the mixtures in the compound plate were transferred to Millipore 384-well FB filter plates via the VELOCITY11® Vprep liquid handler. The filter plate was washed with water 4 times by using the manifold Embla plate washer and dried at 60° C. for 45 min. MicroScint 20 scintillation fluid (30 μl) was added to each well for counting on the Packard TOPCOUNT®. EC$_{50}$ is defined as the agonist concentration that corresponds to 50% of the Ymax (maximal response) obtained for each individual compound tested. The results in Table B were rounded to two significant digits.

TABLE B

| Example No. | GTPγS S1P1 EC50 (nM) | GTPγS S1P3 EC50 (nM) |
|---|---|---|
| 4 | 280 | >62000 |
| 7 | 130 | 630 |
| 8 | 710 | >62000 |
| 9 | 530 | 2200 |
| 12 | 330 | 5900 |
| 16 | 5700 | >62000 |
| 17 | 740 | 1200 |
| 19 | 2200 | 1700 |
| 24 | 3200 | 1300 |
| 26 | 4900 | 16000 |
| 29 | 36 | 430 |
| 32 | 50 | 430 |
| 33 | 67 | 550 |
| 38 | 100 | 2200 |

A smaller value for GTPγS S1P$_1$ EC$_{50}$ value indicated greater activity for the compound in the GTPγS S1P$_1$ binding assay. A larger value for the GTPγS S1P$_3$ EC$_{50}$ value indicated less activity in the GTPγS S1P$_3$ binding assay. The compounds of the present invention, as exemplified by examples in Table B showed GTPγS S1P$_1$ EC$_{50}$ values of 15 μM or lower.

The compounds of the present invention possess activity as agonists of S1P$_1$, and thus may be used in treating, preventing, or curing various S1P$_1$ receptor-related conditions. The surprising activity of the compounds of the present invention indicate their potential use in treating, preventing, or curing autoimmune and inflammatory diseases such as multiple sclerosis, rheumatoid arthritis, inflammatory bowel disease, or psoriasis. Other potential uses of the compounds of the present invention include minimizing or reducing rejection of transplanted organs.

TABLE C

| Example No. | S1P$_1$ Binding IC$_{50}$ (nM) | GTPγS S1P$_1$ EC$_{50}$ (nM) |
|---|---|---|
| 7 | 3.3 | 130 |
| 42 (comparative) | 12,000 | >62,000 |

Table C compares Example 7, a compound in which the oxadiazolyl group and the cyclohexyl group are linked by a C$_2$ alkylenyl group (L$_1$ is —CH$_2$CH$_2$—), and Comparative Example 42, in which the oxadiazolyl group and the cyclohexyl group are bonded directly (corresponding to L$_1$=bond). Example 7 had a S1P$_1$ binding IC$_{50}$ value of 3.3 nM and a GTPγS S1P$_1$ EC$_{50}$ value of 130 nM. In comparison, Example 42 had a S1P$_1$ binding IC$_{50}$ value of 12,000 nM and a GTPγS S1P$_1$ EC$_{50}$ value of >62,000 nM.

What is claimed is:

1. A compound of Formula (I):

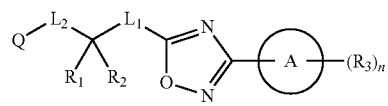

or stereoisomers, N-oxides, or salts thereof; wherein:
Ring A is phenyl, thiophenyl, thiazolyl, pyridinyl, or pyridinonyl;
R$_1$ and R$_2$ together with the carbon atom to which they are attached, form a C$_{4-6}$cycloalkyl substituted with zero to 2 R$_a$;
each R$_3$ is independently:
 (i) F, Cl, C$_{1-4}$alkyl, —CF$_3$, —O(C$_{1-4}$alkyl), —OCF$_3$, —S(O)$_m$(C$_{1-4}$alkyl), and/or —NH$_2$; and/or
 (ii) —CH$_2$A$_1$, —OA$_1$, —OCH$_2$OA$_1$, and/or —CH$_2$SO$_2$A$_1$, wherein A$_l$ is phenyl, pyridinyl, thiazolyl, or imidazolyl substituted with zero to 2 substituents independently selected from F, Cl, —NH$_2$, C$_{1-4}$alkyl, —CF$_3$, C$_{1-4}$alkoxy, and/or —S(C$_{1-4}$alkyl);
L$_1$ is —(CR$_b$R$_b$)$_{2-4}$— or —(CH$_2$)$_{0-2}$O(CH$_2$)$_{1-2}$—;
L$_2$ is a bond;
Q is phenyl substituted with zero to 3 substituents independently selected from F, Cl, C$_{1-3}$alkyl, —CN, —NO$_2$, —NH$_2$, C$_{1-2}$fluoroalkyl, C$_{1-3}$alkoxy, C$_{1-2}$fluoroalkoxy, —NHC(O)(C$_{1-3}$alkyl), —NHC(O)O(C$_{1-3}$alkyl), —NHS(O)$_2$(C$_{1-3}$alkyl), and/or —S(C$_{1-3}$alkyl);
each R$_a$ is independently F, Cl, C$_{1-3}$alkyl, and/or —S(O)$_2$R$_d$; and/or two R$_a$ attached to the same carbon atom form =O;
each R$_b$ is independently H, —CH$_3$, F, Cl, —OH, and/or C$_{1-3}$alkoxy, provided that if one R$_b$ is —OH, then the second R$_b$ attached to the same carbon is not —OH, F, or Cl;
R$_d$ is phenyl substituted with zero to 2 substituents independently selected from F, Cl, —CH$_3$, —CF$_3$, —OCH$_3$, and/or —OCF$_3$;
m is zero, 1, or 2; and
n is zero, 1, 2, or 3.

2. The compound according to claim 1 or stereoisomers, N-oxides, or salts thereof; wherein:
Ring A is phenyl;
L$_1$ is: —(CH$_2$CH$_2$)$_{2-4}$— or —(CH$_2$)$_{1-2}$O(CH$_2$)$_{1-2}$—;

Q is phenyl substituted with zero to 3 substituents independently selected from F, Cl, $C_{1-3}$alkyl, —CN, —NO$_2$, —NH$_2$, —CF$_3$, $C_{1-2}$alkoxy, and/or —OCF$_3$; and
each $R_a$ is independently F, Cl, and/or —CH$_3$.

3. The compound according to claim 1 or stereoisomers, N-oxides, or salts thereof; wherein:
Ring A is thiophenyl, thiazolyl, pyridinyl, or pyridinonyl;
$L_1$ is: —(CH$_2$CH$_2$)$_{2-4}$—;
$L_1$ is: —(CH$_2$CH$_2$)$_{2-4}$—; and
Q is phenyl substituted with zero to 3 substituents independently selected from F, Cl, $C_{1-2}$alkyl, —CN, —NH$_2$, —CF$_3$, —OCH$_3$, and/or —OCF$_3$.

4. The compound according to claim 1 or stereoisomers, N-oxides, or salts thereof; wherein:
each $R_3$ is independently:
(i) F, Cl, $C_{1-4}$alkyl, —CF$_3$, —OCH$_3$, —OCF$_3$, and/or —NH$_2$; and/or
(ii) —CH$_2$A$_1$, —OA$_1$, —OCH$_2$A$_1$, —CH$_2$OA$_1$, and/or —CH$_2$SO$_2$A$_1$, wherein A$_1$ is phenyl, pyridinyl, thiazolyl, or imidazolyl substituted with zero to 2 substituents independently selected from F, Cl, —NH$_2$, $C_{1-2}$alkyl, —CF$_3$, and/or —OCH$_3$;
$L_1$ is —CH$_2$CH$_2$— or —CH$_2$OCH$_2$—; and
Q is phenyl substituted with zero to 3 substituents independently selected from F, Cl, —CH$_3$, —CN, and/or —CF$_3$.

5. The compound according to claim 4 or stereoisomers, N-oxides, or salts thereof; wherein said compound has the structure of Formula (II):

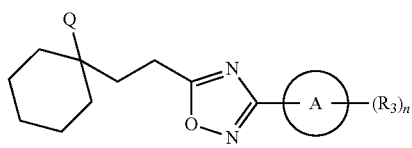

(II)

Q is phenyl substituted with zero to 2 F;
each $R_3$ is independently selected from:
(i) F, Cl, $C_{1-4}$alkyl, —CF$_3$, —OCH$_3$, —OCF$_3$, and/or —NH$_2$; and/or
(ii) —CH$_2$(dichloroimidazolyl), —O(trifluoromethyl pyridinyl), —OCH$_2$(methylthiazolyl), —OCH$_2$(chlorothiazolyl), —OCH$_2$(phenyl), —OCH$_2$(fluorophenyl), —OCH$_2$(chlorophenyl), —OCH$_2$(dichlorophenyl), and/or —CH$_2$SO$_2$(chlorophenyl); and
n is zero, 1, or 2.

6. The compound according to claim 1 or stereoisomers, N-oxides, or salts thereof, wherein said compound is selected from: 3-(5-(2-(1-(3,5-difluorophenyl) cyclohexyl) ethyl)-1,2,4-oxadiazol-3-yl)-6-methyl-2(1H)-pyridinone (1); 4-(5-(2-(1-(3,5-difluorophenyl)cyclohexyl) ethyl)-1,2,4-oxadiazol-3-yl)-2(1H)-pyridinone (2); 3-(3-fluoro-4-methylphenyl)-5-(2-(1-phenylcyclohexyl)ethyl)-1,2,4-oxadiazole (3); 3-(3,5-bis(trifluoromethyl)phenyl)-5-(2-(1-phenylcyclohexypethyl)-1,2,4-oxadiazole (4); 3-(4-fluorophenyl)-5-(2-(1-phenylcyclohexyl)ethyl)-1,2,4-oxadiazole (5); 3-(4-methylphenyl)-5-(2-(1-phenylcyclohexyl)ethyl)-1,2,4-oxadiazole (6); 3-phenyl-5-(2-(1-phenylcyclohexyl)ethyl)-1,2,4-oxadiazole (7); 5-(2-(1-phenylcyclohexyl)ethyl)-3-(3-(trifluoromethyl)phenyl)-1,2,4-oxadiazole (8); 3-(3-methylphenyl)-5-(2-(1-phenylcyclohexyl)ethyl)-1,2,4-oxadiazole (9); 3-(4-chlorophenyl)-5-(2-(1-phenylcyclohexypethyl)-1,2,4-oxadiazol (10); 5-(2-(1-phenylcyclohexyl)ethyl)-3-(4-(trifluoromethyl)phenyl)-1,2,4-oxadiazo le (11); 3-(3,4-difluorophenyl)-5-(2-(1-phenylcyclohexyl)ethyl)-1,2,4-oxadiazole (12); 3-(3-fluoro-4-(trifluoromethyl)phenyl)-5-(2-(1-phenylcyclohexyl)ethyl)-1,2,4-oxadiazole (13); 3-(4-methoxyphenyl)-5-(2-(1-phenylcyclohexyl)ethyl)-1,2,4-oxadiazole (14); 3-(4-tert-butylphenyl)-5-(2-(1-phenylcyclohexyl)ethyl)-1,2,4-oxadiazole (15); 5-(2-(1-phenylcyclohexyl)ethyl)-3-(4-(trifluoromethoxy)phenyl)-1,2,4-oxadiazole (16); 3-(2,4-dichlorophenyl)-5-(2-(1-phenylcyclohexyl) ethyl)-1,2,4-oxadiazole (17); 3-(4-(benzyloxy)phenyl)-5-(2-(1-phenylcyclohexyl)ethyl)-1,2,4-oxadiazole (18); 3-(3,5-dimethoxyphenyl)-5-(2-(1-phenylcyclohexyl)ethyl)-1,2,4-oxadiazole (19); 3-(4-((2-fluorobenzyl)oxy)phenyl)-5-(2-(1-phenylcyclohexypethyl)-1,2,4-oxadiazole (20); 3-(3-(((4-chlorophenyl)sulfonyl)methyl)phenyl)-5-(2-(1-phenylcyclohexyl)ethyl)-1,2,4-oxadiazole (21); 3-(4-((2-methyl-1,3-thiazol-4-yl)methoxy)phenyl)-5 -(241 -phenylcyclohexyl)ethyl)-1,2,4-oxadiazo le (22); 3-(4-((2-chloro-1,3-thiazol-5-yl)methoxy)phenyl)-5-(2-(1-phenylcyclohexyl)ethyl)-1,2,4-oxadiazole (23); 3-(3-((4,5-dichloro-1H-imidazol-1-yl)methyl)phenyl)-5-(2-(1-phenylcyclohexyl) ethyl)-1,2,4-oxadiazole (24); 3-(4-((2,4-dichlorobenzyl)oxy)phenyl)-5-(2-(1-phenylcyclohexyl) ethyl)-1,2,4-oxadiazole (25); 3-(2,5-dimethoxyphenyl)-5-(2-(1-phenylcyclohexyl)ethyl)-1,2,4-oxadiazole (26); 3-(4-((4-chlorobenzyl)oxy)phenyl)-5-(2-(1-phenylcyclohexyl)ethyl)-1,2,4-oxadiazole (27); 3-(2,4-difluorophenyl)-5-(2-(1-phenylcyclohexyl)ethyl)-1,2,4-oxadiazole (28); 4-(5-(2-(1-phenylcyclohexyl)ethyl)-1,2,4-oxadiazol-3-yl)-2-pyridinamine (29); 2-(5-(2-(1-phenylcyclohexypethyl)-1,2,4-oxadiazol-3-yl)pyridine (30); 3-(5-chloro-2-methylphenyl)-5-(2-(1-phenylcyclohexyl) ethyl)-1,2,4-oxadiazole (31); 2-chloro-4-(5-(2-(1-phenylcyclohexyl) ethyl)-1,2,4-oxadiazol-3-yl)pyridine (32); 3-(5-(2-(1-phenylcyclohexyl)ethyl)-1,2,4-oxadiazol-3-yl)-2-pyridinamine (33); 4-(5-(2-(1-phenylcyclohexyl)ethyl)-1,2,4-oxadiazol-3-yl)pyridine 1-oxide (34); 3-(2-methyl-1,3-thiazol-4-yl)-5-(2-(1-phenylcyclohexyl)ethyl)-1,2,4-oxadiazole (35); 2-(4-(5-(2-(1-phenylcyclohexypethyl)-1,2,4-oxadiazol-3-yl)phenoxy)-5-(trifluoromethyl) pyridine (36); 4-(5-(2-(1-phenylcyclohexyl)ethyl)-1,2,4-oxadiazol-3-yl)pyridine (37); 3-(5-(2-(1-phenylcyclohexyl)ethyl)-1,2,4-oxadiazol-3-yl)pyridine (38); 3-methyl-2-(5-(2-(1-phenylcyclohexyl)ethyl)-1,2,4-oxadiazol-3-yl)pyridine (39); and 3-(3-methyl-2-thienyl)-5-(2-(1-phenylcyclohexyl)ethyl)-1,2,4-oxadiazole (40); and 3-(2-chloro-4-methylphenyl)-5-(41-(4-chlorophenyl)cyclobutyl)methoxy)methyl)-1,2,4-oxadiazole (41).

7. A pharmaceutical composition comprising a compound according to claim 1 or stereoisomers or pharmaceutically acceptable salts thereof, and a pharmaceutically acceptable carrier.

* * * * *